(12) United States Patent
Brust et al.

(10) Patent No.: US 9,679,112 B2
(45) Date of Patent: *Jun. 13, 2017

(54) EXPERT-BASED CONTENT AND COACHING PLATFORM

(71) Applicant: Wellclub, LLC, Saint Paul, MN (US)

(72) Inventors: Thomas Edwin Brust, White Bear Lake, MN (US); Phil Kennedy, Eagan, MN (US); Jamal Khan, Redding, CT (US); Jay W. Johnson, Minnetrista, MN (US); Tom Waddell, New Brighton, MN (US)

(73) Assignee: Wellclub, LLC, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/822,980

(22) Filed: Aug. 11, 2015

(65) Prior Publication Data

US 2016/0103921 A1 Apr. 14, 2016

Related U.S. Application Data

(63) Continuation of application No. 13/801,048, filed on Mar. 13, 2013, now Pat. No. 9,110,958.
(Continued)

(51) Int. Cl.
*G06F 17/30* (2006.01)
*G06F 19/00* (2011.01)
(Continued)

(52) U.S. Cl.
CPC .......... *G06F 19/345* (2013.01); *G06F 3/0481* (2013.01); *G06F 3/04842* (2013.01);
(Continued)

(58) Field of Classification Search
None
See application file for complete search history.

(56) References Cited

U.S. PATENT DOCUMENTS

| | | |
|---|---|---|
| 4,853,854 A | 8/1989 | Behar et al. |
| 5,251,126 A | 10/1993 | Kahn et al. |

(Continued)

OTHER PUBLICATIONS

"U.S. Appl. No. 13/772,405, Examiner Interview Summary mailed Apr. 21, 2015", 3 pgs.
(Continued)

*Primary Examiner* — Belix M Ortiz Ditren
(74) *Attorney, Agent, or Firm* — Schwegman Lundberg & Woessner, P.A.

(57) ABSTRACT

Systems and methods for implementing and performing coaching-assisted content delivery and workflows are described. In one example, a goal-based workflow integrates with operations for suggesting and delivering content on behalf of professional users. The operations may be conducted in connection with a subscription or membership to an information service, and various interactions between a client user and a professional user through the information service. In further examples, the information service may track data for the human user, generate suggestions and playlists, manage the accomplishment of goals and logic triggers, and exchange communications, to facilitate the relationship between the professional user and the client user. In other further examples, the information system manages various data values used to provide prompts, reminders, motivators, and other forms of suggested content to the client user.

27 Claims, 28 Drawing Sheets

Related U.S. Application Data

(60) Provisional application No. 61/732,676, filed on Dec. 3, 2012.

(51) Int. Cl.
*G06F 3/0481* (2013.01)
*G06Q 10/10* (2012.01)
*G06F 3/0484* (2013.01)
*H04L 29/08* (2006.01)

(52) U.S. Cl.
CPC .. *G06F 17/30029* (2013.01); *G06F 17/30053* (2013.01); *G06F 17/30386* (2013.01); *G06F 17/30528* (2013.01); *G06F 17/30554* (2013.01); *G06F 17/30598* (2013.01); *G06F 17/30867* (2013.01); *G06Q 10/10* (2013.01); *H04L 67/125* (2013.01); *H04L 67/22* (2013.01); *G06F 19/363* (2013.01)

(56) References Cited

U.S. PATENT DOCUMENTS

| | | |
|---|---|---|
| 5,596,994 A | 1/1997 | Bro |
| 5,933,136 A | 8/1999 | Brown |
| 6,039,688 A | 3/2000 | Douglas et al. |
| 6,059,724 A | 5/2000 | Campell et al. |
| 6,101,478 A | 8/2000 | Brown |
| 6,144,837 A | 11/2000 | Quy |
| 6,240,394 B1 | 5/2001 | Uecker et al. |
| 6,294,999 B1 | 9/2001 | Yarin et al. |
| 6,381,577 B1 | 4/2002 | Brown |
| 6,547,727 B1 | 4/2003 | Hashiguchi et al. |
| 6,697,783 B1 | 2/2004 | Brinkman et al. |
| 7,216,084 B2 | 5/2007 | Brinkman et al. |
| 7,223,235 B2 | 5/2007 | Brown |
| 7,258,666 B2 | 8/2007 | Brown |
| 7,261,690 B2 | 8/2007 | Teller et al. |
| 7,287,031 B1 | 10/2007 | Karpf et al. |
| 7,297,109 B2 | 11/2007 | Brown |
| 7,299,192 B2 | 11/2007 | Luttrell |
| 7,302,398 B2 | 11/2007 | Ban et al. |
| 7,376,700 B1 | 5/2008 | Clark et al. |
| 7,395,216 B2 | 7/2008 | Rosenfeld et al. |
| 7,412,511 B2 | 8/2008 | Curry |
| 7,478,129 B1 | 1/2009 | Chemtob |
| 7,493,264 B1 | 2/2009 | Kelly et al. |
| 7,555,436 B2 | 6/2009 | Brown |
| 7,584,108 B2 | 9/2009 | Brown |
| 7,590,549 B2 | 9/2009 | Brown |
| 7,636,667 B2 | 12/2009 | Brown |
| 7,647,234 B1 | 1/2010 | Ruderman et al. |
| 7,653,556 B2 | 1/2010 | Rovinelli et al. |
| 7,684,999 B2 | 3/2010 | Brown |
| 7,685,000 B1 | 3/2010 | Petit et al. |
| 7,689,437 B1 | 3/2010 | Teller et al. |
| 7,689,440 B2 | 3/2010 | Brown |
| 7,720,855 B2 | 5/2010 | Brown |
| 7,739,124 B1 | 6/2010 | Walker et al. |
| 7,752,056 B2 | 7/2010 | Brown |
| 7,756,722 B2 | 7/2010 | Levine et al. |
| 7,765,112 B2 | 7/2010 | Brown |
| 7,769,600 B2 | 8/2010 | Iliff |
| 7,778,845 B2 | 8/2010 | Brown |
| 7,788,113 B2 | 8/2010 | Fuhrman et al. |
| 7,801,745 B2 | 9/2010 | Walker et al. |
| 7,809,584 B2 | 10/2010 | Morag et al. |
| 7,822,621 B1 | 10/2010 | Chappel |
| 7,822,625 B2 | 10/2010 | Brown |
| 7,827,039 B2 | 11/2010 | Butcher et al. |
| 7,827,040 B2 | 11/2010 | Brown |
| 7,827,042 B2 | 11/2010 | Jung et al. |
| 7,840,420 B2 | 11/2010 | Brown |
| 7,862,506 B2 | 1/2011 | Brown |
| 7,867,165 B2 | 1/2011 | Brown |
| 7,869,852 B2 | 1/2011 | Brown |
| 7,870,249 B2 | 1/2011 | Brown |
| 7,871,376 B2 | 1/2011 | Brown |
| 7,877,274 B2 | 1/2011 | Brown |
| 7,877,276 B2 | 1/2011 | Brown |
| 7,890,346 B2 | 2/2011 | Padron et al. |
| 7,904,530 B2 | 3/2011 | Partridge et al. |
| 7,921,186 B2 | 4/2011 | Brown |
| 7,925,522 B2 | 4/2011 | Brown |
| 7,941,323 B2 | 5/2011 | Brown |
| 7,941,326 B2 | 5/2011 | Brown |
| 7,941,327 B2 | 5/2011 | Brown |
| 7,944,342 B2 | 5/2011 | Sekura |
| 7,944,448 B2 | 5/2011 | Iwamura et al. |
| 7,945,461 B2 | 5/2011 | Sekura |
| 7,955,219 B2 | 6/2011 | Birrell et al. |
| 7,970,620 B2 | 6/2011 | Brown |
| 7,972,247 B2 | 7/2011 | Daikeler et al. |
| 7,979,284 B2 | 7/2011 | Brown |
| 7,985,164 B2 | 7/2011 | Ashby |
| 7,993,267 B2 | 8/2011 | Iliff |
| 8,013,736 B2 | 9/2011 | Derrick et al. |
| 8,015,025 B2 | 9/2011 | Brown |
| 8,015,030 B2 | 9/2011 | Brown |
| 8,015,033 B2 | 9/2011 | Brown |
| 8,015,138 B2 | 9/2011 | Illiff |
| 8,019,618 B2 | 9/2011 | Brown |
| 8,024,201 B2 | 9/2011 | Brown |
| 8,032,399 B2 | 10/2011 | Brown |
| 8,034,294 B1 | 10/2011 | Goldberg |
| 8,036,912 B2 | 10/2011 | Jensen et al. |
| 8,038,577 B2 | 10/2011 | McIntosh |
| 8,055,516 B2 | 11/2011 | Iliff |
| 8,066,514 B2 | 11/2011 | Clarke |
| 8,069,131 B1 | 11/2011 | Luechtefeld et al. |
| 8,073,707 B2 | 12/2011 | Teller et al. |
| 8,075,451 B2 | 12/2011 | Dugan |
| 8,078,492 B2 | 12/2011 | Brown et al. |
| 8,095,522 B2 | 1/2012 | Welti et al. |
| 8,100,757 B2 | 1/2012 | Melendez |
| 8,108,226 B2 | 1/2012 | Barrett |
| 8,109,874 B2 | 2/2012 | Kong et al. |
| 8,131,570 B2 | 3/2012 | Levin et al. |
| 8,140,663 B2 | 3/2012 | Brown |
| 8,160,901 B2 | 4/2012 | Heywood et al. |
| 8,165,893 B1 | 4/2012 | Goldberg et al. |
| 8,170,807 B2 | 5/2012 | Barnett et al. |
| 8,180,592 B2 | 5/2012 | Yuen et al. |
| 8,182,267 B2 | 5/2012 | Katz et al. |
| 8,182,424 B2 | 5/2012 | Heckerman |
| 8,202,202 B2 | 6/2012 | McGlynn et al. |
| 8,234,127 B2 | 7/2012 | Naik et al. |
| 8,277,377 B2 | 10/2012 | Quy |
| 9,037,578 B2 | 5/2015 | Brust et al. |
| 9,110,958 B2 | 8/2015 | Brust et al. |
| 2001/0027403 A1 | 10/2001 | Peterson et al. |
| 2001/0039503 A1 | 11/2001 | Chan et al. |
| 2002/0026333 A1 | 2/2002 | Endou |
| 2002/0055857 A1 | 5/2002 | Mault |
| 2002/0055859 A1 | 5/2002 | Goodman et al. |
| 2002/0072932 A1 | 6/2002 | Swamy |
| 2002/0087358 A1 | 7/2002 | Gilbert |
| 2002/0128861 A1 | 9/2002 | Lau et al. |
| 2002/0133377 A1 | 9/2002 | Brown |
| 2002/0183598 A1 | 12/2002 | Teraura et al. |
| 2002/0184056 A1 | 12/2002 | Tsuboi |
| 2003/0014279 A1 | 1/2003 | Roman et al. |
| 2003/0061065 A1 | 3/2003 | Keeley |
| 2003/0061215 A1 | 3/2003 | Messina |
| 2003/0065561 A1 | 4/2003 | Brown et al. |
| 2003/0101076 A1 | 5/2003 | Zaleski |
| 2003/0182161 A1 | 9/2003 | Vanderlei et al. |
| 2004/0131997 A1 | 7/2004 | McGuire et al. |
| 2004/0176666 A1 | 9/2004 | Chait |
| 2004/0215491 A1 | 10/2004 | Clark et al. |
| 2004/0242973 A1 | 12/2004 | Tanabe et al. |
| 2004/0243443 A1 | 12/2004 | Asano et al. |
| 2005/0095628 A1 | 5/2005 | Krempin et al. |
| 2005/0113650 A1 | 5/2005 | Pacione et al. |
| 2005/0117527 A1 | 6/2005 | Williams et al. |

(56) References Cited

U.S. PATENT DOCUMENTS

| | | |
|---|---|---|
| 2005/0240434 A1 | 10/2005 | Wooten et al. |
| 2005/0240438 A1 | 10/2005 | Day |
| 2005/0240444 A1 | 10/2005 | Wooten et al. |
| 2005/0283385 A1 | 12/2005 | Hunkeler et al. |
| 2005/0283386 A1 | 12/2005 | Powers et al. |
| 2006/0004611 A1 | 1/2006 | Brown |
| 2006/0010014 A1 | 1/2006 | Brown |
| 2006/0026036 A1 | 2/2006 | Mahmood |
| 2006/0064322 A1 | 3/2006 | Mascarenhas et al. |
| 2006/0189853 A1 | 8/2006 | Brown |
| 2006/0224416 A1 | 10/2006 | Lloyd et al. |
| 2006/0235722 A1 | 10/2006 | Brown |
| 2007/0005395 A1 | 1/2007 | Singh |
| 2007/0016446 A1 | 1/2007 | Brown |
| 2007/0021984 A1 | 1/2007 | Brown |
| 2007/0055549 A1 | 3/2007 | Moore et al. |
| 2007/0061167 A1 | 3/2007 | Brown |
| 2007/0072156 A1 | 3/2007 | Kaufman et al. |
| 2007/0100595 A1 | 5/2007 | Earles et al. |
| 2007/0190501 A1 | 8/2007 | Brown |
| 2007/0260511 A1 | 11/2007 | Bender, II |
| 2007/0282842 A1 | 12/2007 | Messinaq |
| 2008/0004902 A1 | 1/2008 | Leong-fern et al. |
| 2008/0103814 A1 | 5/2008 | Fabius et al. |
| 2008/0103855 A1 | 5/2008 | Hernandez et al. |
| 2008/0124689 A1 | 5/2008 | Williams et al. |
| 2008/0126276 A1 | 5/2008 | Williams et al. |
| 2008/0126277 A1 | 5/2008 | Williams et al. |
| 2008/0140449 A1 | 6/2008 | Hayes |
| 2008/0162352 A1 | 7/2008 | Gizewski |
| 2008/0168032 A1 | 7/2008 | Criou et al. |
| 2008/0172246 A1 | 7/2008 | Larkin |
| 2008/0183757 A1 | 7/2008 | Dorogusker et al. |
| 2008/0243543 A1 | 10/2008 | Jung |
| 2008/0287748 A1 | 11/2008 | Sapounas et al. |
| 2008/0318678 A1 | 12/2008 | Stivoric et al. |
| 2009/0005009 A1 | 1/2009 | Marsili |
| 2009/0012988 A1 | 1/2009 | Brown |
| 2009/0030732 A1 | 1/2009 | Jung |
| 2009/0043613 A1 | 2/2009 | Jung et al. |
| 2009/0069643 A1 | 3/2009 | Quy |
| 2009/0070141 A1 | 3/2009 | Jolley |
| 2009/0112617 A1 | 4/2009 | Jung et al. |
| 2009/0118593 A1 | 5/2009 | Jung |
| 2009/0119154 A1 | 5/2009 | Jung |
| 2009/0131089 A1 | 5/2009 | Micali et al. |
| 2009/0132275 A1 | 5/2009 | Jung et al. |
| 2009/0193082 A1 | 7/2009 | Brown |
| 2009/0199230 A1 | 8/2009 | Kumar et al. |
| 2009/0312668 A1 | 12/2009 | Ieuthardt et al. |
| 2010/0010829 A1 | 1/2010 | Moore et al. |
| 2010/0063833 A1 | 3/2010 | Mahoney |
| 2010/0150384 A1 | 6/2010 | Waldmann |
| 2010/0235776 A1 | 9/2010 | Brown |
| 2010/0250497 A1 | 9/2010 | Redlich et al. |
| 2011/0152635 A1 | 6/2011 | Morris et al. |
| 2011/0172497 A1* | 7/2011 | Ruby .................... G06Q 50/22 600/300 |
| 2011/0209037 A1 | 8/2011 | Yoon et al. |
| 2011/0276451 A1 | 11/2011 | Busse |
| 2012/0011139 A1 | 1/2012 | Drissi et al. |
| 2012/0149972 A1 | 6/2012 | Moore |
| 2012/0221345 A1 | 8/2012 | McClure et al. |
| 2012/0272278 A1 | 10/2012 | Bedi |
| 2013/0124218 A1 | 5/2013 | Masloski et al. |
| 2014/0100955 A1 | 4/2014 | Osotio et al. |
| 2014/0156308 A1 | 6/2014 | Ohnemus et al. |
| 2014/0156645 A1 | 6/2014 | Brust et al. |
| 2014/0156646 A1 | 6/2014 | Brust et al. |
| 2014/0156676 A1 | 6/2014 | Brust et al. |
| 2014/0157171 A1 | 6/2014 | Brust et al. |

OTHER PUBLICATIONS

"U.S. Appl. No. 13/772,405, Final Office Action mailed Jul. 9, 2015", 23 pgs.
"U.S. Appl. No. 13/772,405, Non Final Office Action mailed Jan. 7, 2015", 22 pgs.
"U.S. Appl. No. 13/772,405, Response filed May 7, 2015 to Non Final Office Action mailed Jan. 7, 2015", 22 pgs.
"U.S. Appl. No. 13/772,697, Examiner Interview Summary mailed Dec. 17, 2014", 3 pgs.
"U.S. Appl. No. 13/772,697, Non Final Office Action mailed Sep. 3, 2014", 12 pgs.
"U.S. Appl. No. 13/772,697, Notice of Allowance mailed Jan. 20, 2015", 7 pgs.
"U.S. Appl. No. 13/772,697, Response filed Dec. 23, 2014 to Non Final Office Action mailed Sep. 3, 2014", 16 pgs.
"U.S. Appl. No. 13/801,048, Examiner Interview Summary mailed Mar. 27, 2015", 3 pgs.
"U.S. Appl. No. 13/801,048, Non Final Office Action mailed Nov. 25, 2014", 8 pgs.
"U.S. Appl. No. 13/801,048, Notice of Allowance mailed Jun. 5, 2015", 7 pgs.
"U.S. Appl. No. 13/801,048, Response filed Mar. 25, 2015 to Non Final Office Action mailed Nov. 25, 2014", 15 pgs.
"U.S. Appl. No. 13/801,315, Non Final Office Action mailed Apr. 6, 2015", 20 pgs.
"U.S. Appl. No. 13/801,315, Response filed Jul. 1, 2015 to Non Final Office Action mailed Apr. 6, 2015", 12 pgs.
"Lift", Powered by Tumblr, [Online]. Retrieved from the Internet: <URL: https://web.archive.org/web/20121116235453/http:/blog.lift.do/, (Nov. 16, 2012), 17 pgs.
"U.S. Appl. No. 13/772,405, Notice of Allowance mailed Aug. 28, 2015", 8 pgs.
"U.S. Appl. No. 13/772,405,Response filed Aug. 10, 2015 to Final Office Action mailed Jul. 9, 2015", 16 pgs.
"U.S. Appl. No. 13/801,315, Notice of Allowance mailed Sep. 15, 2015", 10 pgs.
"U.S. Appl. No. 14/713,276, Preliminary Amendment Filed Aug. 27, 2015", 11 pgs.

* cited by examiner

My Suggestions > Playlists > Suggestion Playlist Title > Suggestion Content Title

1/4 | 64 X 64

Suggestion Content Title

⊙ 24 hours  ↻ Repeat  1 reminders
15 min     3 times   2 motivators

Description of Suggestion Content.

| Timing | Motivators | Reminders |

Suggestion Timing

▨ Reminder (drag and drop to add/remove)

■ Motivator (drag and drop to add/remove)

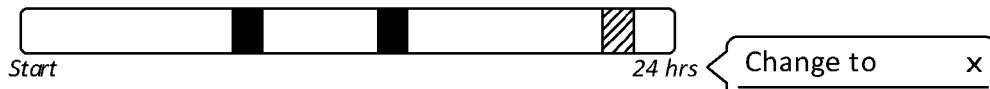

Start                                      24 hrs

Change to    x
[ 24 hours  |v ]

When to send the suggestion

| Sun | Mon | Tue | Wed | Thu | Fri | Sat |

[ 3:00 PM |v ]  Note: This is based on the member's time zone (PST, MST, CST, EST)

Repeat

Repeat every: [ 1 |v ] weeks

Repeat on: ☐ S  ☐ M  ☐ T  ☐ W  ☐ T  ☐ F  ☐ S

Ends: ⦿ Never
      ○ After [    ] occurrences
      ○ On [    ]

Suggestion: ☑ Same
            ☐ Similar
            ☐ Different

Summary:

Cancel   [ Done ]

*FIG. 7F*

Variations of Communication Timing

Legend

1-7 = Communication (suggestions, motivators, reminders, prompts, chat, etc.)

= Amount of time

800

Example 1  1 2 3 4 5 6 7

Example 2  1 2   3      4 5  6       7
(different intensity, delay)

Example 3  7 3 5  4 6 6 6 6  6 2  1           1
(different sequence, frequency, and intensity)

Example 4  1  2   3 4 5 6         7
(multiple threads)  3   3 4  6       7
                                       3

EXPERT-BASED CONTENT AND COACHING PLATFORM

CROSS-REFERENCE TO RELATED APPLICATIONS

This application is a continuation of U.S. application Ser. No. 13/801,048, filed Mar. 13, 2013, which claims the benefit of U.S. Provisional Patent Application Ser. No. 61/732,676, filed Dec. 3, 2012, which is incorporated by reference herein in its entirety. This application is related to pending United States patent application Ser. No. 13/772,697, titled "CONTENT SUGGESTION ENGINE," and filed Feb. 21, 2013; and Ser. No. 13/772,405, titled "GOAL-BASED CONTENT SELECTION AND DELIVERY," and filed Feb. 21, 2013; the disclosures of which are incorporated by reference herein in their entireties.

TECHNICAL FIELD

Embodiments pertain to techniques and systems for content selection and management. Some embodiments relate to the use of expert-based content and coaching mechanisms in an information system to select, suggest, recommend, and deliver content to particular human subjects based on an environmental goal or determined conditions of the human subjects.

BACKGROUND

Various data services select or recommend content for display to users. For example, in the self-help setting, existing data services may provide tips, recommendations, and focused content to assist a subject human user with goal-based outcomes such as exercise goals, weight loss, smoking cessation, medical therapy, and the like. Some of these data services provide recommended content to a user in response to user-indicated preferences, user-indicated activity history, or manual user requests for content. Other data services rely on an expert human user to determine which content is most appropriate for delivery to the subject human user to achieve a goal-based outcome.

To the extent that the existing data services provide automated recommendations or selections of content, the timing, delivery, and substance of content from these data services is determined by complex predetermined rules and attributes, or other selections influenced by manual human intervention. For example, recommendations may be hard-coded in a content delivery system to deliver suggestive content at scheduled intervals, or in response to the user's manual indications that a certain accomplishment has or has not been reached. Additionally, intervention from expert human users is time consuming for both the expert human user and the subject human user, and often does not connect the right information from the expert human user to the subject human user with the most valuable content at the most appropriate time.

Existing systems and techniques do not provide real-time recommendations and content selections without extensive programming or human oversight. Further, the workflows involved with existing content delivery systems call for extensive human selection and specification of content, and are not fully automated, responsive, or adaptive to user needs.

BRIEF DESCRIPTION OF THE DRAWINGS

FIG. 7B illustrates a graphical user interface provided for displaying reviews and ratings of a content suggestion in an expert-based content workflow according to an example described herein.

FIG. 7D illustrates a graphical user interface provided for displaying expert-based content suggestions from a plurality of experts in an expert-based content workflow according to an example described herein.

FIG. 7F illustrates a graphical user interface provided for displaying a content suggestion playlist having varying communication timings in an expert-based content workflow according to an example described herein.

DETAILED DESCRIPTION

Figure 1:
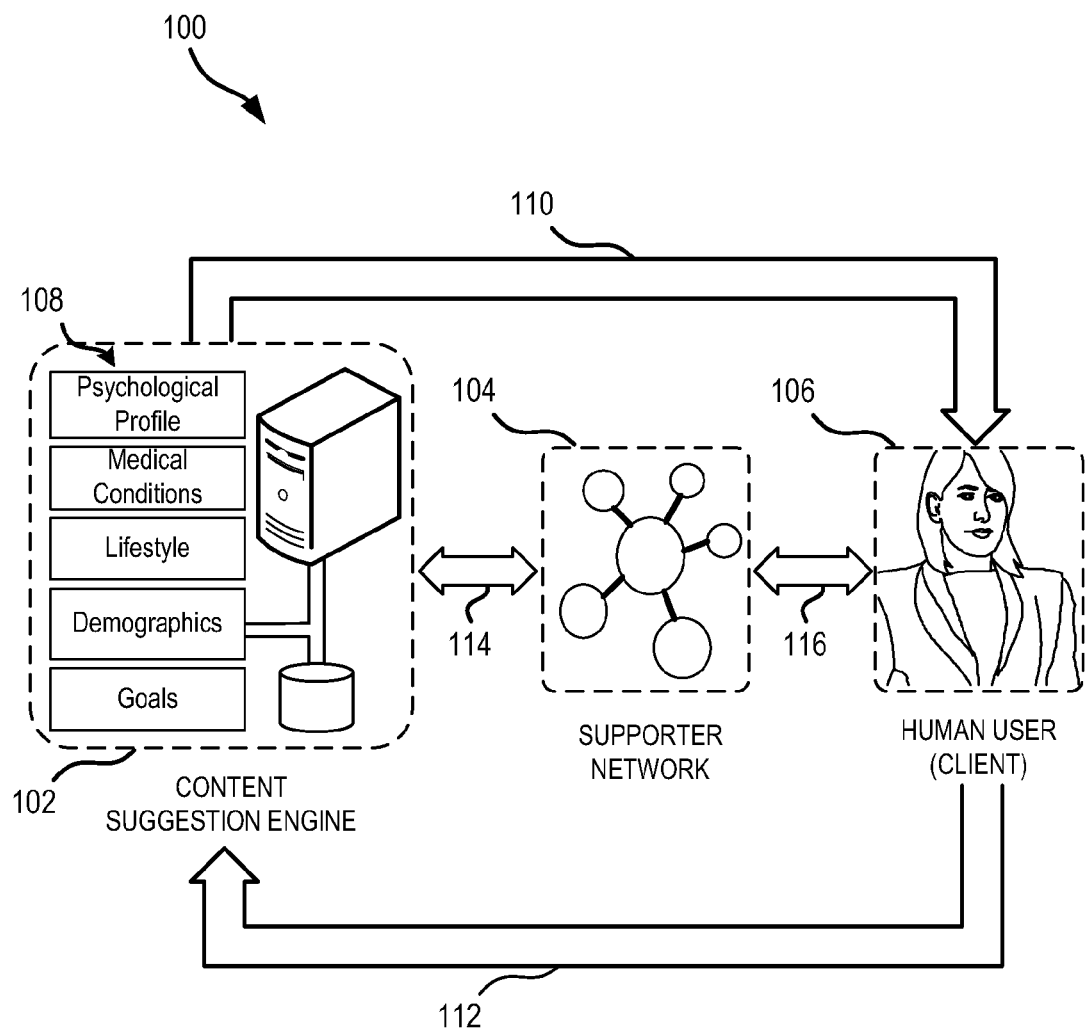
FIG. 1 illustrates an information flow diagram of interaction with an example information system and a content suggestion engine according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

The present disclosure illustrates various techniques and configurations to enable a professional user to select and present content from an information system, for individual and multiple human client users. This content is selected to be relevant to goal-based activities of the respective human client users, for example, from a single professional user to coach multiple subject users at the same time to achieve some goal. The interaction techniques and systems described herein enable a professional user to replicate in-person coaching styles, and provide appropriate content to assist achievement of the goal, through related content and suggested actions. The integration of user interfaces and user communication platforms described herein further may facilitate communications using social networks and portable communication mediums, to provide additional availability and delivery of content from a professional user to multiple client users in a variety of settings.

In one example, an internet-hosted information service offers content to client users through a series of dynamically changing user interfaces. For example, widgets hosted in an interactive webpage or software application may be used to collect, display, and deliver relevant and timely communication, suggestions, and content to and from a user. The information service may be used to directly interact and implement aspects of a goal-based workflow with a subject human user, while also facilitating interaction during the goal achievement with other humans or agents, including professional users. Professional users, as used herein refers to persons such as experts, coaches, trained supporters, and other like persons capable of providing advice and direction to address a particular problem or work towards a certain goal.

The following examples describe various scenarios where a subject client user obtains content from a professional user (with such content generally referred to herein as "expert content"). It will be understood that expert content may originate from any number of professional users, including those not having a direct relationship with particular users. However, the model described herein enables a variety of types of professional users to replicate in-person coaching styles, and provide advice, feedback, tailored content, and other variations of coaching assistance to particular users (especially at times when the user is in greatest need of help). For simplicity of reference, the following examples generally refer to a "professional" or "expert" who provides "expert content," but it will be understood that the techniques are not limited to experts or persons with particular recognized expertise. Rather, expert users would include a variety of professional users offering assistance and coaching and expert content would include a variety of types of content from such users.

The following examples of expert-based coaching activities and coaching content may be used to enhance goal-based workflows facilitated by an information system. As further described herein, goal-based workflows may integrate with various evaluations that dynamically assess a user's current state and receptivity to achieving an action or goal. The goal-based workflows may be exposed through a series of user interfaces that involve social aspects and communications, including interaction with a professional user. In addition to professional user assistance and expert content, various circles of personal influence in a connected group (e.g., trusted sets of friends, called "supporters") may be leveraged to keep a user motivated to achieve lifestyle improvements in a fun and inviting manner.

The coaching and supporter interactions may be integrated with features of a social network and social network communications to engage support from friends and professional users. Such supporters may publicly or privately encourage a user to accomplish various activities and achieve goals. A series of scripted or self-generated directives, "destinations," and action playlists may also be used to direct a client onto the path of incremental improvements towards achievement of an ultimate goal. Such goal-based workflows provide numerous opportunities for helpful professional user assistance.

Information System Configuration

The expert-based coaching and content applications described by the present disclosure may be performed in connection with automated receipt, processing, and delivery of relevant content from an electronic information system. The information system, as further described herein, may encourage human interaction with a series of goal-based workflows and goal-based processing activities that deliver relevant content to encourage human activity and progress towards an ultimate goal. Relevant content may be provided in a push or pull manner, on schedule or in response to determined conditions, and manually or automatically from the information system, in accordance with the following techniques.

The computing systems and platforms encompassed by the present disclosure include a mobile or web-based social networking information service, interacting with a suggestion engine, that is used to motivate the human user to change behavior (such as healthy lifestyle choices and activities that are likely to lead to a positive health outcome) through a persistent intelligent coaching model. The information service may provide intelligent decision making and reinforcement of certain content and content actions, to facilitate encouragement or motivation that increases the likelihood of change in human behavior to achieve the goal. In particular, the information service focuses on encouraging a human user to complete a series of discrete, separate actions or activities (small goals) that in combination will help achieve a larger overall goal. For example, in a weight loss setting, this may include a series of tens, hundreds, or thousands of discrete diet and exercise actions that in combination will help the human user achieve a weight loss goal.

In conjunction with operations of the suggestion engine, the information service may adapt to learn a user's behavior patterns and offer personalized, relevant, or timely suggestions, motivations, or other directed content to help the human user achieve the goal. The information service also may enable peer and professional support for a human user by creating and maintaining human connections relevant to the goal, such as through establishing social networking connections and social networking interactions customized to the goal. As the social network or the behaviors of the human user change, the information service may adapt to alter the actions, motivations, or other directed content to remain relevant, personal, or timely to the human user. In this fashion, the information service is intended to cause behavior changes of the human users, through promotion to achieve the user's goals with social encouragement by friends, family, or supporters, or expert users, in addition to personal motivations reinforced with reminders, or new structures in their living environment, such as may be helpful in altering habits to achieve the goal.

The information service may include various applications and corresponding user interfaces to be viewed by the human user and supporters of the human user to encourage beneficial interactions between the human user and the supporters. These interactions, which may be driven by suggested content and suggested content delivery types or timings, are used to cause activities that lead to the intended behavior change(s) in a human user. Accordingly, the content suggestion engine acts in a larger environment of an "intelligent" information system that provides appropriate messages and content selections to the human user and supporters at the right time.

FIG. 1 illustrates an information flow diagram of interaction with an example information system 100 configured for providing content (e.g., motivations, recommendations, suggestions, facts, or other relevant material) to human users. The information system 100 may include a suggestion engine 102, participation from a supporter network 104 of various human or automated users (including expert and other professional users), and participation from a subject human user (further referred to herein as a "client") 106, with the information system 100 supporting a plurality of client users.

The suggestion engine 102 may be configured to make decisions to deliver relevant content dynamically (e.g., at the proper time, in the proper context, and with the proper communication medium) using data conditions 108 maintained for the client 106. The data conditions 108 maintained for the client 106 may include information such as: one or more goals of the client 106; demographic information such as gender, age, and familial information; medical information such as medical conditions, medical history, and medical or physical restrictions; a psychological profile and other psychological information such as personality type, daily routines or habits, emotional status, likes and dislikes; and available external devices (e.g., smart phone or smart phone applications, smart weight scales, smart TV, video game systems, etc.); client-desired coaching programs and models (e.g., diet style, exercise focus, or mental health); information relevant to discrete activities, such as present or scheduled locations of the client 106, and time to accomplish activities; information relevant to the goal, such as time to achieve the goal, difficulty of achieving the goal; and like information for conditions relevant to the human user, supporters of the human user, or the overall goal.

The specific content selection operations of the suggestion engine 102 are directed to change the behavior of the client 106, such as to help the client 106 achieve a defined or derived goal with a series of content messages that invoke action by suggested activities and events. Delivery of the content may be provided directly from the suggestion engine 102 to the client 106 with a content delivery flow 110. With the content delivery flow 110, the suggestion engine 102 may query the client 106, such as by periodically or randomly querying, to gain information and feedback that may affect what content is delivered to the client 106. Responses by the client 106 may be provided back to the content suggestion engine 102 through a content feedback flow 112 to indicate the results of such querying or feedback.

The suggestion engine 102 may also provide indirect content delivery flows 114, 116 through a supporter network 104, to enable the supporter network 104 to provide content to the client 106 at appropriate times. Specifically, the suggestion engine 102 may indirectly provide content selections to the client 106 using indirect content delivery flow 114, and orchestrate resources of the supporter network 104 by engaging influential persons (e.g., family, friends, experts, other professional users that influence the client 106) to forward or deliver the content.

The supporter network 104 may also facilitate interaction from professional users such as healthcare providers, nutritionists, personal trainers, psychologists, or behavior coaches. Such interaction from professional users in the supporter network 104 may be used to proactively guide personalized and critically timed suggestions (e.g., such as by sending a message to the client 106 that encourages a specific activity), or persistently offer coaching, guiding, motivating, or focusing actions and content for encouraging the client 106 to complete actions to achieve or make progress on the goal.

Additionally, members of the supporter network 104 may generate and provide suggestions back to the suggestion engine 102, directly or with crowdsourcing-type mechanisms distributed among a plurality of persons. For example, a supporter may directly author suggestions that are sent to the human user, or edit, modify, or unify suggestions with slight modifications for user with human users. Based on the effectiveness of the content created by the supporter network 104, a pool of suggestions may be created.

Thus, the supporter network 104 may be used to generate or forward content selected by the suggestion engine 102, using indirect content delivery flow 116. For example, the suggestion engine 102 may provide a supporter of the supporter network 104 with pre-formatted action content that may be sent directly from the supporter to the client 106 using a recognized communication medium, such as by forwarding and customizing a text message, an email message, a social network message, and the like. Suggestions directly received from members of the supporter network 104 are more likely to reduce barriers or excuses and empower the client 106 to take action that will help achieve their goals. Feedback may also be provided back to members of the supporter network 104 from the client 106 (such as a confirmation that the client 106 performed the activity, a message that the client 106 enjoyed the suggestion, a message asking for support to perform the activity, and the like).

The suggestion engine 102 may communicate with the supporter network 104 and the client 106, such as to obtain information about the client 106 or provide messages to the client 106 or to the supporter network 104. The supporter network 104 may personalize the message and send it to the client 106, such as shown in FIG. 1. By having the client 106 receive the message from the supporter network 104 the message may have more impact, and potentially be more motivating, than if it came directly from the suggestion engine 102.

Suggestion Content Types and Delivery

Appropriate messages, multimedia, and other content delivered to the client 106 from or on behalf of the information system 100 are referred to herein as "suggestion content," as may be selected and produced by the content suggestion engine 102. Suggestion content may include content from one or more messages that the client 106 and supporter network 104 receive that are collectively intended to cause human attention and cause the client 106 to perform some action. The suggestion content may be tailored and customized to be appropriate to the client 106, time, and individual intended actions. The suggestion content may include a variety of formats, such as content that indicates greetings, actions, motivations, prompts, reminders, and rewards. Further, the suggestion content may be delivered and interacted with according to particular goal-based workflows or rule sets.

As used herein, suggestion content may include content delivered to the client 106 intended to cause an action related to an ultimate goal. Suggested action content sent to the client 106, may be constructed from content that includes an action statement, and a pre statement or a post statement.

As used herein, motivational content is a specific subset of suggestion content that is intended to improve the likelihood of the client 106 performing a suggested action by appealing to some human interest. Motivational content may be embodied by: various prompts that include a request of the client 106 or supporter network 104 for a response; reminders that include a statement that reminds the client 106 or a supporter from the supporter network 104 that an action on their part is due; rewards that include statements provided to the client 106 or supporter that are congratulatory or explain something being given to the client 106 or supporter; supporter messages that include content specifically intended for the supporter.

Content provided by the information system 100 may be stored and maintained in structured and unstructured form. Unstructured content may include suggestion content not yet edited, tagged, or final reviewed; whereas structured content may include content that has been edited, tagged, and reviewed, and is ready for use by the suggestion engine 102 (as further illustrated with reference below to FIGS. 2A and 2B).

Content may be tagged for use in defined retrieval operations. Such tagging may include a psychological assessment matching. A client 106 may be asked to take assessments for engagement, receptivity, or social style. The content may be tagged in such a way that the information system 100 matches the client 106 with the style of the content suited for them. This may "personalize" the interactions between the information system 100 and the client 106, such as to provide a more effective or engaging environment. The information system 100 may provide content for each of eating, movement (e.g., actions to physically accomplish), and self-view. The tags may provide this information.

The tagging of data may include "behavior change" tagging. A current behavior change theory promotes a combination of "sources of behavior change" that promote a higher probability of changing people's behavior. These sources of behavior change include items that improve an individual's intrinsic/extrinsic motivation and aptitude, group factors and power to cause behavior change, and environmental factors and power to cause behavior change. Presenting suggestions that fit in multiple behavior change areas may be more effective than presenting suggestions in just one or a few of the areas. Additionally, the client 106 may fill out a lifestyle questionnaire, which determines, such as by using Boolean logic, different "problems" that the client 106 may have. Content may be tagged with these problems, such as to tag content that relates to the problem. The client 106 may work on the problem by choosing specific suggestions or playlists tagged with that problem.

In one example use of a suggestion engine 102, the client 106 is the person that the information system 100 is intended to help; the supporter network 104 may include one of the persons providing aid to the client 106—this person could be a team member, friend, family member, or a professional user/other expert such as personal trainer. Thus, overall users of the suggestion engine 102 may include any person using the information service (and accompanying applications, websites, and services), including the client 106, supporters in the supporter network 104, an administrator, and the like.

The information system 100 facilitates interaction with the client 106 and supporters in the supporter network 104, such as encouraging clients and supporters to interact in the social network, to accompany several types of content. Content may be created that gives clients and supporters specific actions to do, and this content may be delivered in a way that encourages the supporter or client 106 to do the action. The content may be designed to be delivered to the client 106 either directly or through the supporter. A plurality of action statements providing respective suggested actions may be presented to the client 106 for participation. Other types of content may be used to increase the probability of the client 106 performing the suggested actions.

Figure 2A:
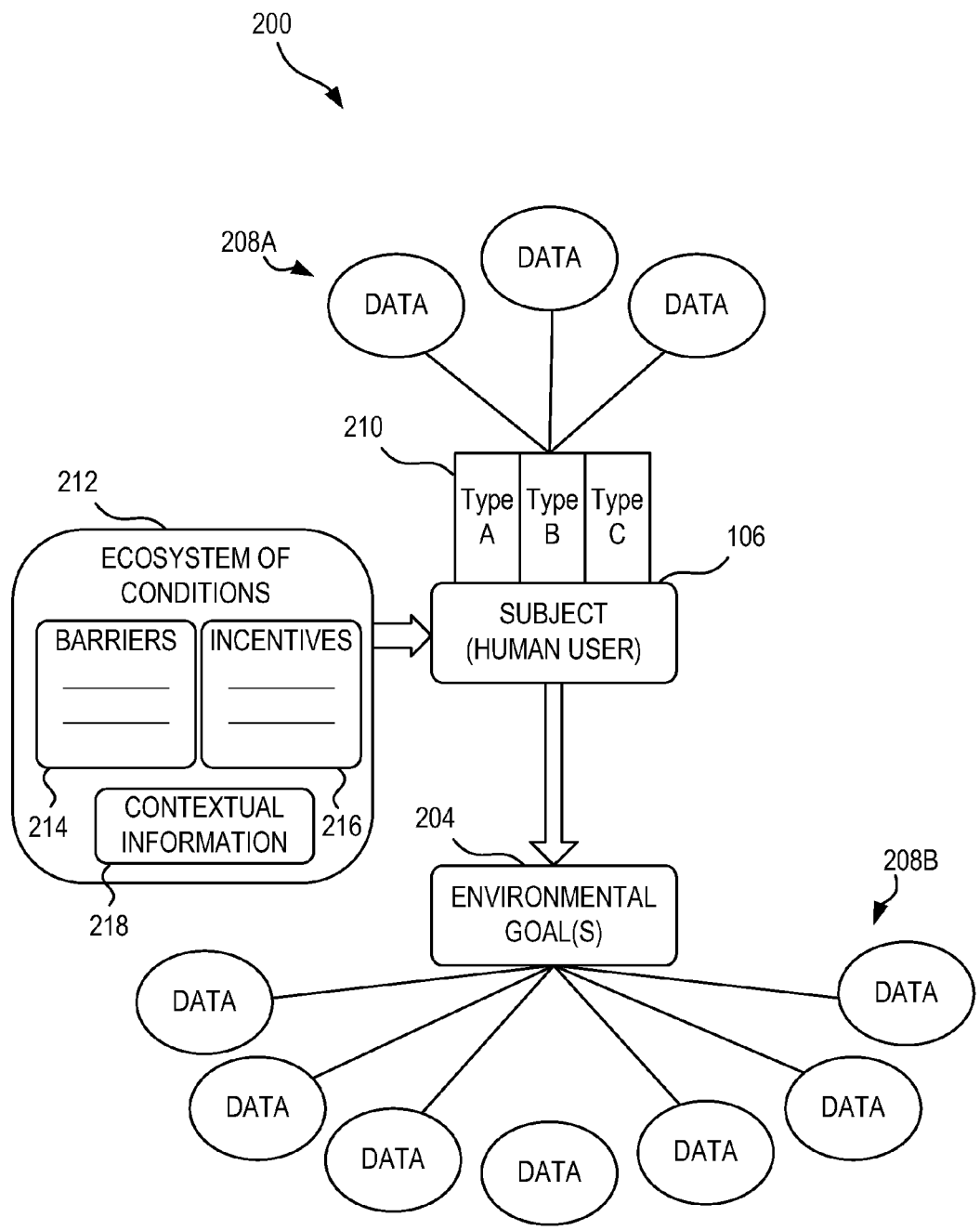
FIG. 2A illustrates an information flow diagram of data operations for factoring activities relevant to an environmental goal according to an example described herein.

FIG. 2A illustrates an information flow diagram of an example of data operations 200 of the suggestion engine 102. Data 208A and 208B, illustrated as various inputs, may be provided in a structured format. Structured data in one example is unstructured data that has undergone a formalization, structuring, categorization, and tagging process in the information system 100 illustrated in FIG. 1. The data operations 200 serve to map data 208A to a personality or behavior type 210 or characteristic of a human user such as the client 106, and an ecosystem of conditions 212 is factored to produce appropriate data 208B that addresses one or more environmental goals 204.

Data input for operations 200 of the suggestion engine 102 may originate from a variety of data sets and data types, but not all data types and data inputs may impact a human subject to attain a particular goal at a particular time. Data 208A may be provided from client personal data, such as location, the psychological state, lifestyle, occupation, relationship status, or coaching style, among others, collected or determined for the client 106. A client's behavior type 210, such as caregiver, colleague, competitor, authoritarian, optimist, skeptic, fatalist, activist, driver, analytical, amiable, expressive, or combinations thereof, may be inferred or otherwise determined from the data 208A (and changed or adapted as appropriate using contextual user information 218 or data 208B).

An ecosystem of conditions 212, including barriers 214 to and incentives 216 for achieving the one or more environmental goals 204 may be determined. The ecosystem of conditions 212 generally reflects information items that the information system 100 is aware of, and relevant factors to achieve success. This may include data such as the time of day, client location, medical records of the client 106, and like information or conditions that affect the client 106.

Barriers 214 considered with the ecosystem of conditions 212 may include the client 106 having a physical ailment, such as a bad knee or asthma, not having a phone, not having supporters, does not like working out, cannot afford the services, having a busy schedule, medical conditions (such as allergies or taking medications), among others. Incentives 216 considered with the ecosystem of conditions 212 may include things that the client 106 likes (e.g., brand name shoes or specific music), peer pressure, a good feeling gained from performing some activity (e.g., working out), a discount on goods or services provided, or an upcoming event (e.g., a half marathon). The data 208A, 208B and the ecosystem of conditions 212 may be determined through obtaining answers to questions, such as through answers to episodic questions posed to the client 106 (the episodic questions resulting at determined times, places, or contexts). The ecosystem of conditions 212 further may provide contextual user information 218 to provide additional data to help interpret or understand the barriers 214, incentives 216, or the data 208A, 208B.

The data 208B may be directly or indirectly related to the one or more environmental goals 204. The data 208B may include a reward for achieving the goal(s) 204 (e.g., kudos), a type of diet to be followed, a reason for wanting to achieve the goal, or a date to achieve the goal by, among others. The environmental goal(s) 204 may include physical activity goals, such as to lose a certain amount of weight, change a habit, such as to quit smoking, biting fingernails, workout a specific number of times in a period of time, or to achieve a physical challenge such as running a marathon or climbing a mountain, among others.

The one or more environmental goals 204 are not necessarily limited to a central, ultimate goal (such as losing weight, or stopping smoking), but may include a number of subordinate or associated goals (such as developing healthy habits, a positive self-image, or confidence or enjoyment of the goal-reaching process) that help achieve the ultimate goal in a positive fashion. Thus, the environmental goals 204 may be broader than a single goal and may include a number of additive, complimentary, or interrelated actions and results that produce beneficial outcomes and experiences for the client 106.

Different humans have preferred ways of being talked to and interacted with. The information system 100 may facilitate the client 106 taking several questionnaires that show these preferences. A personality style may be inferred or determined from answers to questions in the questionnaires. The personality styles may indicate a client's receptivity (e.g., the preference for a certain tone of message); engagement (e.g., a bias towards immediate action versus thoughtful consideration when presented with a challenge to change); or social style (e.g., an intersection of assertiveness and responsiveness). The content may be designed to fulfill all these preferences.

Figure 2B:
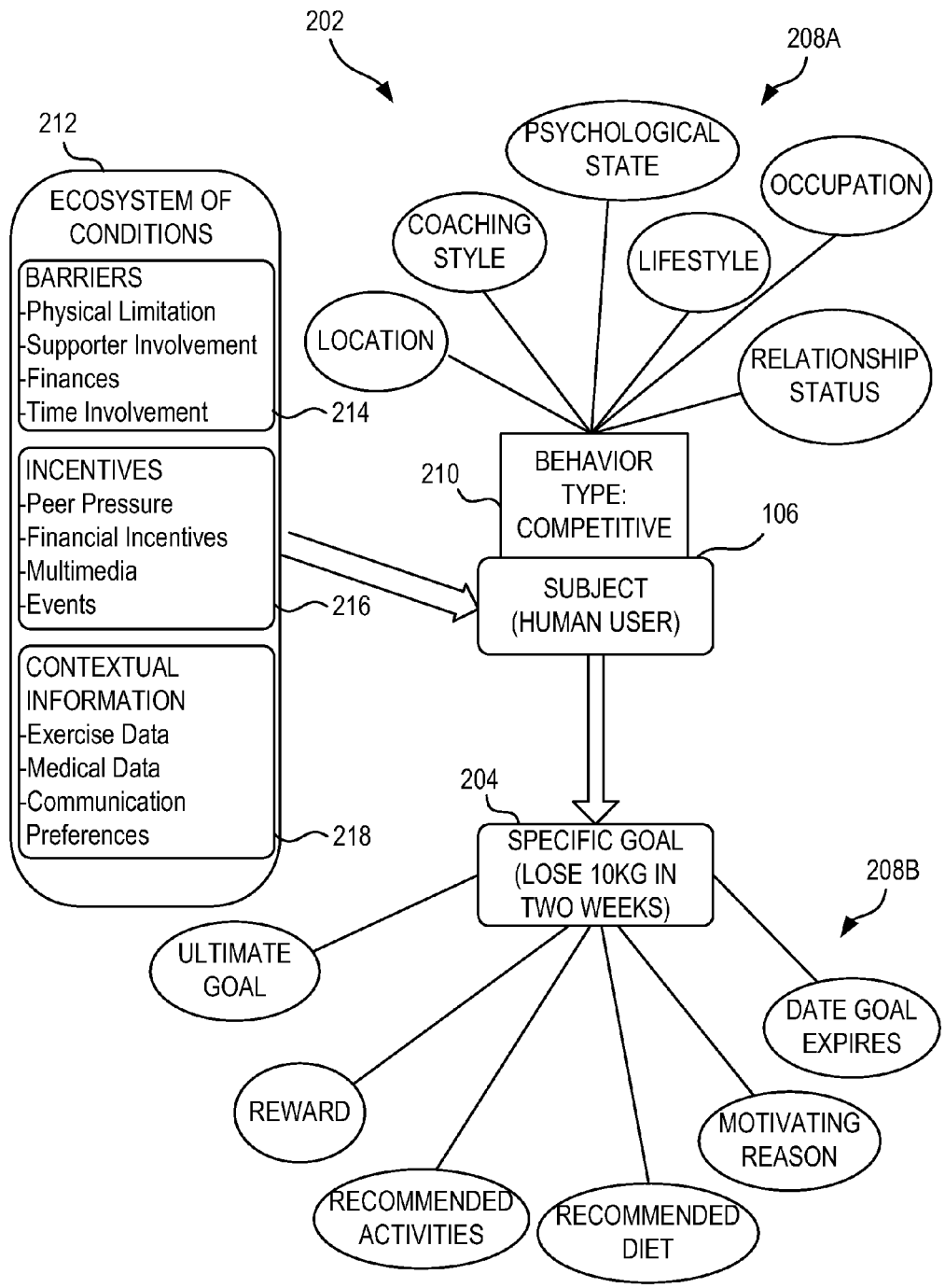
FIG. 2B illustrates an information flow diagram of data operations for factoring activities relevant to a specific physiological goal according to an example described herein.

FIG. 2B provides an illustration of an information flow diagram of an example of data operations 202 of the suggestion engine 102 applied to a specific weight loss goal 204 (e.g., to lose 10 kilograms in two weeks). In particular, the data operations 202 illustrate the association of specific data points 208A with the client 106 and the client's behavior type 210, the association of specific data points 208B with a specific goal 204, and the provision of an ecosystem of conditions 212 that affect the client 106.

As illustrated in FIG. 2B, some of the specific data points 208A associated with the client 106 and the client's behavior type 210 might include data related to: the client's location; the client's preferred coaching style; the client's current or historical psychological state; the client's lifestyle; the client's occupation; or the client's relationship status. As shown, the client's behavior type 210 is classified as "competitive", which may serve to filter or weight usage for some of the data points 208A.

As also illustrated in FIG. 2B, some of the conditions that affect the client 106 include various barriers, incentives, and contextual information data points. The data points relevant to the client 106 may include barriers such as physical limitations; limitations on supporter (including professional user) involvement; limited finances; or limited time involvement. The data points relevant to the client 106 may also include incentives such as peer pressure; financial incentives; multimedia (e.g., a favorite song); and events and enjoyable activities. The data points relevant to the client 106 may also be contextual user information 218 such as exercise data (such as data provided from physiological monitoring device); medical data (such as provided from a medical device, a psychological monitoring device, or medical records); and communication preferences (to accomplish more effective communications). Each of these conditions may provide further classifications and conditions. For example, communication preferences may be established not just for the type of communications, but also for the particular sender (because some clients may be more receptive to communications from particular people).

As also illustrated in FIG. 2B, some of the specific data points associated with the specific weight loss goal 204 might include data related to: the ultimate goal; reward status or reward history; recommended activities and history of progress toward recommended activities; recommended diet and history of progress toward recommended diet; motivating reason(s); and timeliness such as the date that the goal expires.

The content and goal-based workflows delivered from the information system 100 may not only be customized to the specific goal or the ultimate goal, but may also be customized to the personality style, barriers, incentives, contextual information, behavior type, and preferences of the client 106. Each of the various data values maintained in the ecosystem of conditions 212 and the data points 208A, 208B may serve to direct the content, timing, availability, and communication methods of the goal-based workflows and workflow results.

Series-Based Goal Actions

Figure 3:
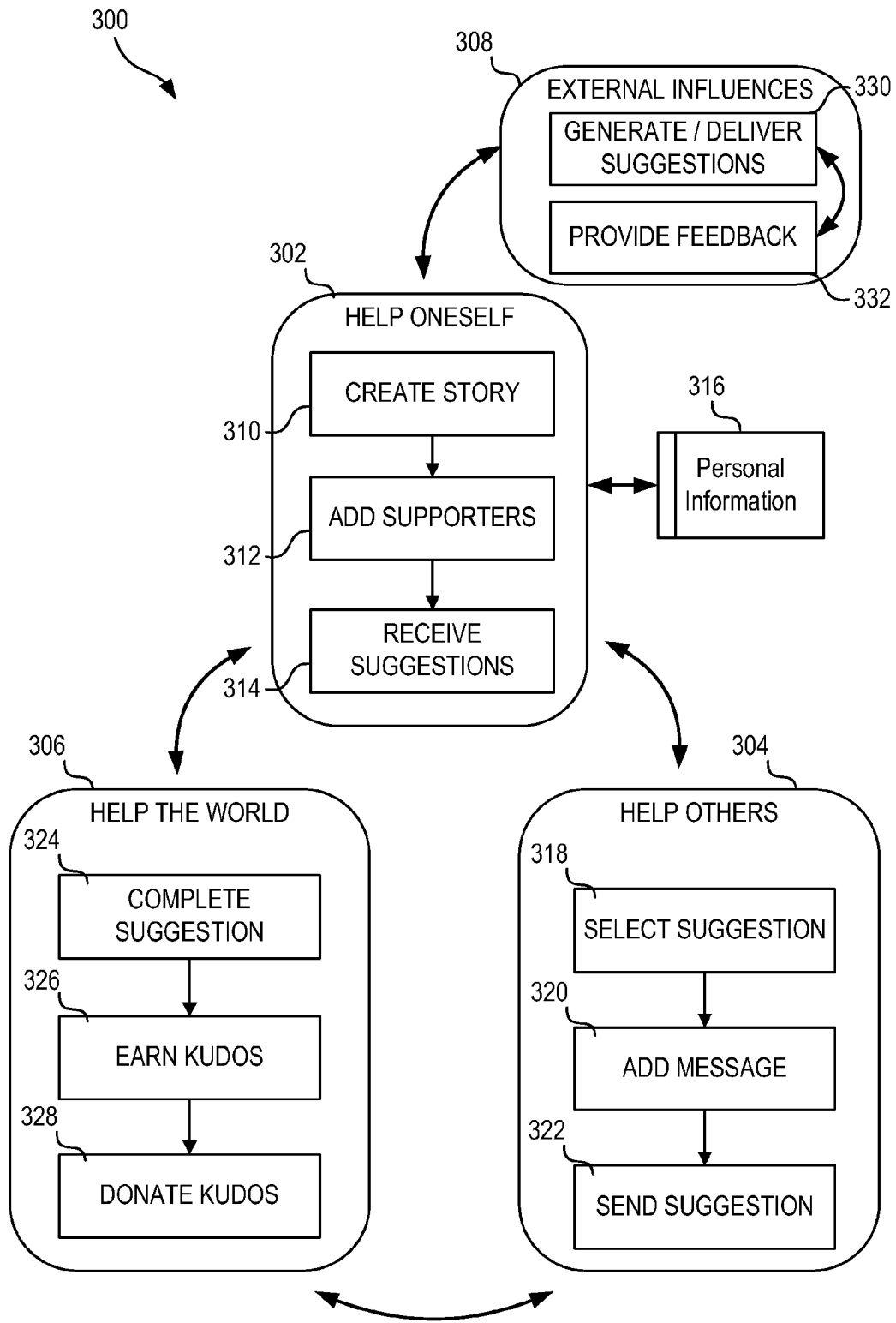
FIG. 3 illustrates an overview of goal-based workflows integrated with an information system according to an example described herein.

FIG. 3 provides an illustration of a framework 300 for a series of integrated goal-based workflows according to examples described herein. Within the framework 300 a user can help oneself (operation 302), help others within the system (operation 304), or can help others outside the system—help the world (operation 306). These and other aspects of the user's activity may also be affected by outside/external influences (operation 308).

Helping oneself may include creating a story (operation 310), adding supporters (operation 312), and receiving suggestions (operation 314) from other users, such as supporters. Creating a story (operation 310) may include indicating or otherwise providing personal information (data 316). Personal information (data 316) may include likes and dislikes, demographic information, medical conditions, goals, lifestyle, or a psychological profile, among others. Helping others may include selecting a suggestion (operation 318), adding a message to the suggestion (operation 320), and sending the suggestion to the user (operation 322). The suggestion can be an encouraging message or some other form or personalizing the suggestion to the user.

Helping the world may include a user completing a suggestion (operation 324), earning kudos (operation 326) (a reward currency) for completing the suggestion, and donating the kudos (operation 328) to a charity or other altruistic destination. The interaction between the user activity (such as helping oneself (operation 302)) and the receipt of external influences (operation 308) may include various suggestions generated or delivered by one or more third parties (operation 330), including professional users, and the one or more third parties providing feedback (operation 332), content, or other input to improve operation of the information system 100.

Coaching Platform Features

The information system 100 may be adapted to include functionality that enables a professional user (e.g., an expert) to provide content to subject users, individually and as appropriate groups. The ability to contact multiple subject users from a single interaction may enable a professional user to manage a larger number of clients while maintaining personal attention. For example, an expert user may wish contact multiple subject users at the same time with a common message, such as to wake up all of their clients with a prompt "Time to get out of bed. How are you feeling today?" The data collected from this interaction may guide special attention needed for specific clients during that day.

The coaching functions in the information system 100 enable direct one-on-one and one-to-many coaching interactions without requiring a physical presence from the professional supporter. The specific content interactions provided through use of the information system 100 can be used to motivate the individual clients to stay on task while facilitating incremental revenue opportunities for the professional user.

Features provided from coaching and expert advice mechanisms and operations in the information system 100 may include, but are not limited to:

A one-to-many service platform, so a member base is scalable, while providing communications to large numbers of members.

Providing access to specific groups of members, that may be may be filtered by profile types, various afflictions, and special needs.

Customized pricing and bundling of services to users of various conditions, based on the client's desired interactions. For example, different prices may be offered for the professional user's offering of: content bundles, playlists, and programs, in-person meetings, or support and coaching through internet and web-based platforms.

Creation and management of referrals and referral incentives, such as a referral list of in-bound sales leads for members, and passes for referrals and user recommendations (e.g., earn a free month of support if you invite three friends to join you).

Creation and management of trigger logic for in-person meetings or other personal attention (e.g., to identify when the client has a bad day, or didn't complete a certain number of suggestions in a row) to generate incremental revenue. Further, the trigger logic can be used to supplement real-world meetings and coaching activities, and used to evaluate results from the real-world meeting.

Creation and management of a professional profile for the professional user, such as a biography, publications, postings, reviews, prices, offerings, expertise, certifications, and the like. Likewise, the professional profile may offer access to an encompassing and consumable member profile which allows the professional user to modify features of his or her coaching style, intensity, and direction.

Management of billing and collections from the client to facilitate payments to the professional user. For example, various incentive offers and payment options such as free trials and modifiable payment tiers and cycles may be offered and managed by the professional user.

Suggestions, ideas, and guidance for how to effectively coach, probe, and contact the user through web and mobile platforms or other interactions with the information system. This may include offering feedback on the professional user's coaching activities (from automated techniques or from other professional users and mentors).

Use of multiple communication mediums, such as web, text, smartphone, to motivate, push, prod, and coach a client towards his or her personalized goal with relevant communications. The communications may be integrated with an integration or visualization of real-time data from a client's personal hardware monitoring devices to verify response to the communications.

Around-the-clock contact and data stream from clients and data services, including mobile access to client progress and billing functions.

Advertisement and promotions. For example, a professional user may become a featured professional of the week/month/year—featuring an individual or group of professionals as a featured provider on a web or mobile service.

These and other relevant coaching functions enable interactions from a professional user with a variety of members to achieve positive results towards goals and activities. For example, in a healthcare coaching scenario, such coaching functions enables healthcare professionals or health/fitness coaches to motivate, support, monitor, and coach the client 106 to make appropriate lifestyle changes, towards a goal such as stopping smoking, losing weight, controlling diabetes, recovering from a cancer diagnosis, and the like.

The information system 100 may collect data from a variety of client hardware monitoring devices that monitor the client activity, for processing, integration, and repackaging of such data for use by the professional user. The information system may provide the professional user to allow the professional user to generate enhanced motivation and support responses and content, to encourage the client to stay on task in attaining goals.

The information system 100 may also provide clients with the ability to rate and review professional users, to provide feedback and input on suggestions and content that is helpful or unhelpful. In addition, the information system 100 may provide the professional users with useful statistics and indications of user responses to particular suggested content or actions by the professional user.

The information system 100 may also provide clients with the ability to find, sort, and purchase services from the professional users, based on the client's profile, need, location, or other criterion. The information system 100 may also provide the ability to match the client to a particular professional user on demand or in response to a determined condition. For example, a user may choose identify a professional user from a listing of available professional users, sorting the listing of professional users by performance results (integrity rating, member reviews), and specific service offerings (such as exercise, nutrition, psychology, diabetes management, and the like).

The information system 100 may also provide members with the ability to utilize multiple communication mediums with skilled and knowledgeable professional users such as healthcare professionals and/or health coaches. This can enable a healthcare professional or health coach to provide advice to hundreds or thousands of clients on a scheduled or as-needed basis.

Coaching Based on Member Profiles

The information system 100 may provide a consumable, encompassing profile for client users, utilizing real-time elements to customize the user experience and content provided. For example, content may be provided to a specific client based on an indication of how the client is feeling today, the weather at the client's location, the GPS location of the client, and others).

Such profile information may also be utilized by a professional user to customize content and make professional evaluations relevant to the client user. By making the data consumable to the professional user (and other users such as an expert supporter), the professional supporter can make accurate and tailored decisions on how to effectively coach the individual.

Figure 4:
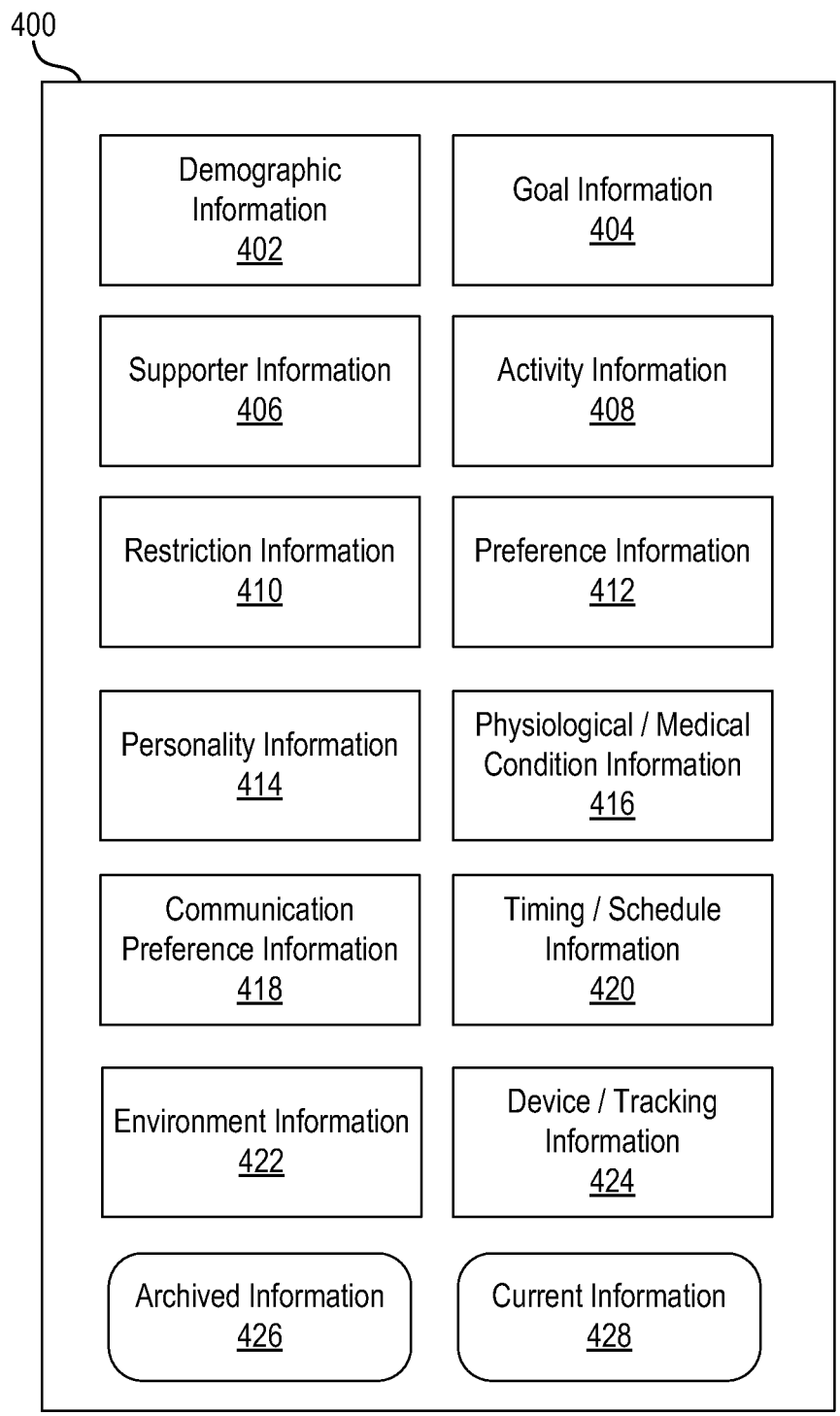
FIG. 4 illustrates a data diagram of member profile information used in connection with expert-based content selection and delivery techniques according to an example described herein.

FIG. 4 illustrates a data diagram of member profile information 400 for a client user that may be used in connection with expert-based content selection and delivery techniques according to one example. For example, the member profile information 400 may be provided to a professional user or used within operations of an information system, such as the information system 100. The data values included and maintained in the member profile information 400 for a client user, such as client 106, may include:

Demographic information 402. This may include, for example, age, location, ethnicity, education level, income of the client 106.

Goal information 404. This may include information related to the specific goal(s) set or determined for the client 106, and progress on the goal(s) as determined by the information system 100.

Supporter information 406. This may include, for example, the number of supporters, level of support and integrity from friends, family, co-workers, and other professional supporters, other subscriptions, and like information.

Activity Information 408. This may include information on lifestyle and relevant activities of the client 106, such as information to identify a stay at home mother of three, versus a business woman spending a large amount of time traveling.

Restriction information 410. This may include information on personal restrictions of the client 106 such as food allergies, injuries, physical limitations, and the like.

Preference information 412. This may include a preferred cuisine(s) or diet styles (e.g. low carb, low calorie, vegan, etc.), or preferred exercise types based on seasons, equipment access and gym membership.

Personality information 414. This may include information related to personality type and preferred communication style, and data obtained from personality assessments.

Physiological and Medical Condition information 416. This may include information on other physical or psychological conditions of the client 106 (such as diabetes, smoking, cardiovascular rehab, depression, and the like).

Communication preference information 418. This may include information on the communication medium preferences or privacy settings for the client 106.

Timing and Scheduling Information 420. This may include information on relevant times and schedules where particular content or activities would be most relevant (or not needed) by the client 106 (for example, information indicating that the client works night shifts as a nurse, rather than a standard daytime office job).

Environment Information 422. This may include information on the user's locale, physical environment home environment, work environment, and factors that may make it harder or easier to accomplish a certain goal.

Device/Tracking Information 424. This may include information collected from medical, exercise, or tracking devices, which provides data that that can be useful for monitoring or coaching purposes.

Archived Information 426 and Current Information 428 data sets. Archived Information 426 may be used to archive or store previous states of the various information fields, such as what was the client's mood or state at a past point in time. Current Information 428 may provide a current data set of the state of the information fields, such as the user's current mood or receptivity to certain activities. Thus, the Current Information 428 is configured to be dynamic and change over time, in response to the client 106.

The information system may be configured to utilize the member profile information 400 to control relevant content and content deliveries provided by the professional user. For example, the information system 100 may alert both the client 106 and the professional user to problematic conditions, triggered when the user did not perform some action, a time expires, or the like. Further, a detected medical scenario such as an eating disorder, depression, or the like may alert the client 106 to visit a doctor or seek medical assistance. Under certain circumstances, the coaching and the professional user's assistance will not address the issue, so the information system can prompt the member to opt from the coaching services and seek medical assistance.

Within various user interfaces, progress tracking for the client 106 may be provided. Interfaces may also allow a particular client 106 to share their profile, progress, and goals with their supporters so proactive coaching can be enabled. The professional user may have access to some or all of this information, to inform the professional user what the client 106 is telling to others and is experiencing.

Coaching techniques may be implemented in any number of automated fashions by the information system 100, as a result of behavior signatures (e.g., detected user behavior) where proactive action is needed. For example, a detected behavior may occur when a goal (e.g., a "destination") is not met, a suggestion is uncompleted, there is a lack of communication or lack of friend support between a client and a user, or when other areas of inactivity and prompting are detected in the information system.

A personality profile stored in the personality information 414 may provide additional, granular information based on a psychological assessment. The personality information 414 may be used to provide the professional user with an overall assessment of the client 106, to provide guidance of how to coach the client 106 through a lifestyle change.

Figure 5:
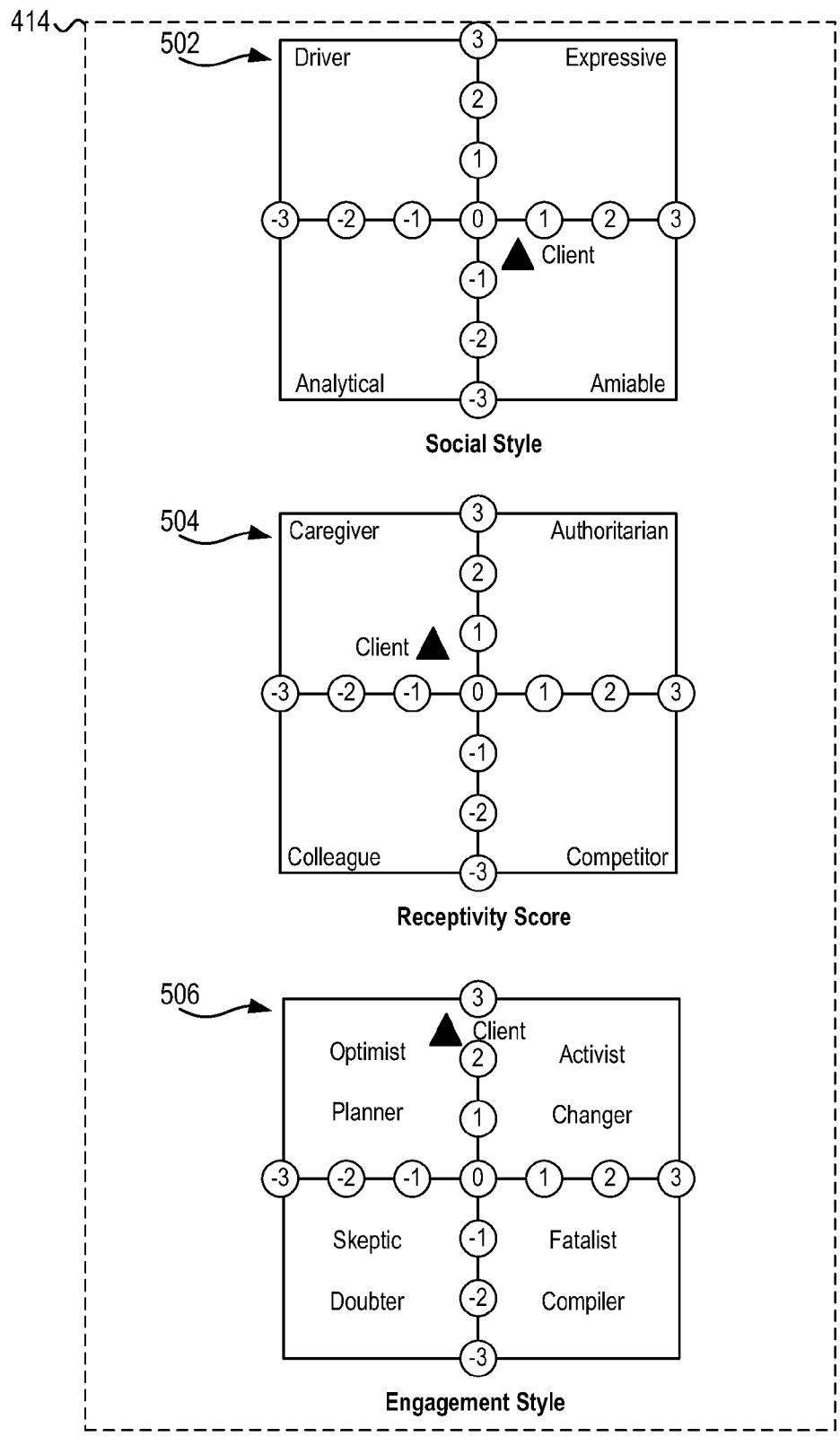
FIG. 5 illustrates a series of personality assessments captured in member profile information used with expert-based content selection and delivery techniques according to an example described herein.

FIG. 5 illustrates an example series of personality assessments captured in member profile information (e.g., member profile information 400), featuring example personality information 414 for use in expert-based content selection and coaching. FIG. 5 specifically illustrates a charting of personality profiles 502, 504, 506 produced from one or more psychological assessments, providing an example consumable personality assessment that can be used by the professional user to effectively coach a client user.

FIG. 5 also illustrates a comparison between different assessments. For example, a social style profile 502 may chart a client at one quadrant in a personality assessment graph, whereas a receptivity score profile 504 and an engagement style profile 506 may chart a client at different quadrants in the personality assessment graph. The example personality profile (e.g., maintained in personality information 414) shows that the evaluated client tends to be slightly amiable (nice, easy to get along with), would prefer a slightly more sensitive coaching style (caregiver), and is very able/willing to make changes in her life (optimist, planner). Such information would be useful to a professional user in crafting specific messages relating to changing behaviors, without offering the messages that push the client too far, too fast.

Workflows and Playlists for Providing Professional User Content

The workflows and goals performed in connection with the information system 100 may be implemented with specific strategies and accomplishments to be Specific, Measurable, Attainable, Relevant/Realistic, and Time-bound. As used herein, the "overall goal" may be an environmental goal or result that may be achieved through performance of the strategies or accomplishments by the client 106. The overall goal may be further divided or segmented into time-based or activity-based goals, such as a series of short term goals, intermediate goals, and long term goals.

The client 106 may set the overall goal (within appropriate conditions and business rules), while the information system 100 may provide smaller goals to measure progress towards the overall goal. The overall goal may be a more abstract concept (e.g., "feel better, be healthier, and lose weight") while the time- or activity-based goal may be more specific and quantifiable. Specifically, the time- or activity-based goal may be quantifiable in order to reach some measurable health goal such as: an amount of weight or body measurement lost; a reduction in smoking a number of cigarettes; a self-measurement on a scale of 1 to 10; an assessment by a medical professional; and the like.

The time- or activity-based goal may be provided with a start and end date. When a goal is met, and another is chosen, the start date (by default) may be established from the end date of the previous goal. In some examples, a client 106 may change the start date. Business rules may be established for achieving the time or activity-based goal within a period of time. For example, in a weight loss setting, if the amount of weight that can be lost in a healthy manner in a given timeframe (such as a maximum of 5 kilograms per week) exceeds the "healthy" rate, the client 106 may be prompted to either push back the end-date or reduce the amount of weight to be lost. Business rules may also be applied to automatically adjust and change the goal as appropriate.

In some examples, the client 106 may set the long-term goal, and the information system 100 responds by providing short-term and intermediate goals to measure progress, and establishing satisfaction of the long-term goal from the short-term and intermediate goals. The short-term and intermediate goals may be provided through use of suggested action and suggested action messages, with the performance of the various suggested actions resulting in an increment of progress towards the ultimate goal. The suggested action and goals are therefore structured to allow specific, quantifiable measurements and results (such as success or failure).

Individual suggestions and suggested actions may be linked together to create playlists or programs. For example, as a comparison to a chemistry-like composition, just as atoms are organized together to create molecules and molecules strung together to create large structures with a specific purpose, individual suggestions and playlists of suggestions combine to create programs with a unique purpose and flavor.

A playlist is a set of suggested actions (each suggested action being introduced to the user through suggested content) that may be presented to the client 106 as a single "set of suggested actions", individually or as part of a short-term goal, intermediate goal, or long-term goal. Providing a playlist can make user actions to choose or select actions less frequent, and provide a short term context for the client 106. The client 106 may want repetition, variety, to concentrate on a particular area, to see progress in a particular area, or to be generally healthy. Playlists may be designed to link suggested actions together to create a coordinated effort that may consider the desires of the client 106.

The playlist may be chosen as a specific item by the client 106. The playlist may include suggested actions over a period of time, such as a day, week, ten days, months, quarter, year, etc. The client 106 may wish to choose a (somewhat) coordinated effort that is longer than a single action. For example, making sure they eat a healthy breakfast for one week. The playlist feature may allow the client 106 to choose this as a single item. Each suggested action in the playlist may be set for specific times as designated in the playlist (e.g., every x period).

A playlist may be linked as part of a larger program. A program can be: 1) a designation of a specific type of suggested action by keywords (e.g., Mayo Clinic diet, weight watchers diet, etc.), where the suggestion engine 102 preferentially chooses actions or playlists to present to the client 106 as a function of the keywords; or 2) a set of playlists presented in a series, such as a series that has a defined objective (for example, eat a good breakfast for four (4) weeks, which may include suggested actions for both purchasing the materials for a good breakfast, such as oatmeal, as well as allowing enough time to eat it before starting the day's other activities).

Professional User Coaching Tools

The information system 100 may provide various features and functions to assist data collection and content delivery. This may provide a professional user with the ability to control multiple aspects of the goal-based workflow and goal-based interactions, including when particular content is delivered to a client, and the defined triggers to provide such content. The professional user may also utilize the information system 100 to provide communications over a variety of mediums, enabling the professional user to chat, send images, send videos, monitor the member, and provide suggestions (including through multimedia, URLs, timing components, and the like).

Figure 6A:
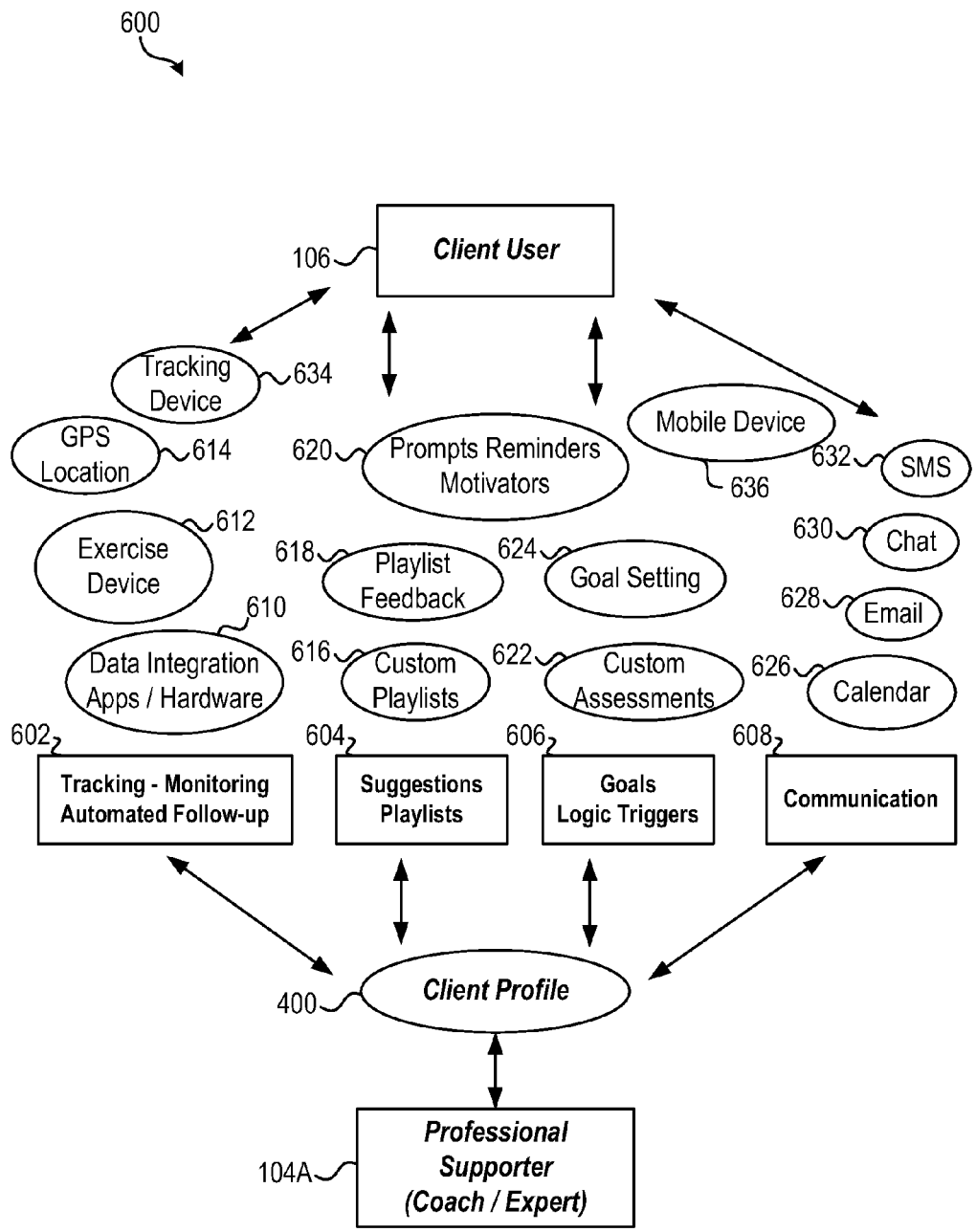
FIG. 6A illustrates uses of member profile information and supporter coaching tools in connection with expert-based content selection and delivery techniques according to an example described herein.

FIG. 6A provides an illustration of member profile information and supporter coaching tools 600 used in connection with expert-based content selection and delivery techniques of the information system 100. As shown, a professional supporter 104A (a coach, expert, or other professional user) accesses a client profile of the information system (e.g., member profile information 400) to utilize various tools and functions (for example, to convey information and activities towards the client user, the client 106).

In a first example, the information system may utilize information in the client profile to provide tracking, monitoring, and automated follow-up on suggestions 602 for delivery to the client 106. The tracking operations may be provided through interface to other technologies, and data integration with various software applications and hardware devices 610. One example hardware device is an exercise tracking device 612 configured to track daily activity (e.g., tracking a client user's walk using an accelerometer, pedometer, GPS, and the like). The client user's GPS location 614 may provide further information on the habits of the client user and the client user's habits, likes, and amount of activity. In other examples, the data integration may occur through a customized app running on the client user's smartphone (e.g., mobile device 636). Other tracking devices 634 including medical devices may be used to collect and provide relevant tracking and monitoring data.

In a second example, the information system may utilize information in the client profile 400 to provide suggestions and playlists 604 to the client 106. This may be provided by pushing suggestions through other supporters, attempting to leverage other relationships to communicate information through the client user's existing supporter relationships. For example, custom playlists 616 may be established to provide custom information from the professional supporter 104A to the client. The client may provide feedback and compliance information back to the professional supporter 104A through the use of playlist feedback 618. This interaction may be provided through the communication mediums described herein, for example, the mobile device 636.

The suggestions and playlists 604 may be integrated with various prompts, reminders, and motivators 620 to deliver the content to the client 106. For example, custom playlists 616 may include of suggestions that are triggered by logic based on various inputs including the custom assessments 622 and the goal setting 624. The prompts, reminders, and motivators 620 may be associated with custom responses defined by the professional supporter 104A, including specific actions to respond to user behavior. For example, a professional supporter 104A may "blow the whistle," "yell," "coach one-on-one," "publicly embarrass," or perform like actions to provide motivation to the client 106.

In a third example, the information system may provide mechanisms to manage goals, logic triggers, and like conditions related to use of the goals. For example, the custom assessments 622 may provide questionnaires to determine the current state of the client user. These mechanisms may also be integrated with goal setting 624 (which may be referred to as a "Destination") and automated tracking of the client user's progress towards the goal.

In a fourth example, the information system may provide various communication mediums 608 to facilitate communication between the professional supporter 104A and the client 106. These may include SMS 632, chat 630, email 628, calendar integration 626 (e.g., to schedule in-person meeting and integrate to other calendar services), phone communications, or communications through interfaces to the Information System 100. In addition, communication may include prompts (providing a two-way communication eliciting response from the user) or a "sales representative"-type call for inquiries on the status of the client user.

The supporter coaching tools 600 may be used to provide a professional user such as the professional supporter 104A with access to scalable client base in need of their expertise. A professional supporter 104A may choose to build teams of clients that they are suited to help, and send playlists to clusters of networks, rather than reaching out to individual clients. In addition, the professional supporter 104A may be able to provide similar or the same content playlists to groups of clients, receiving ratings and feedback to determine which users are most receptive to the coaching and content.

Figure 6B:
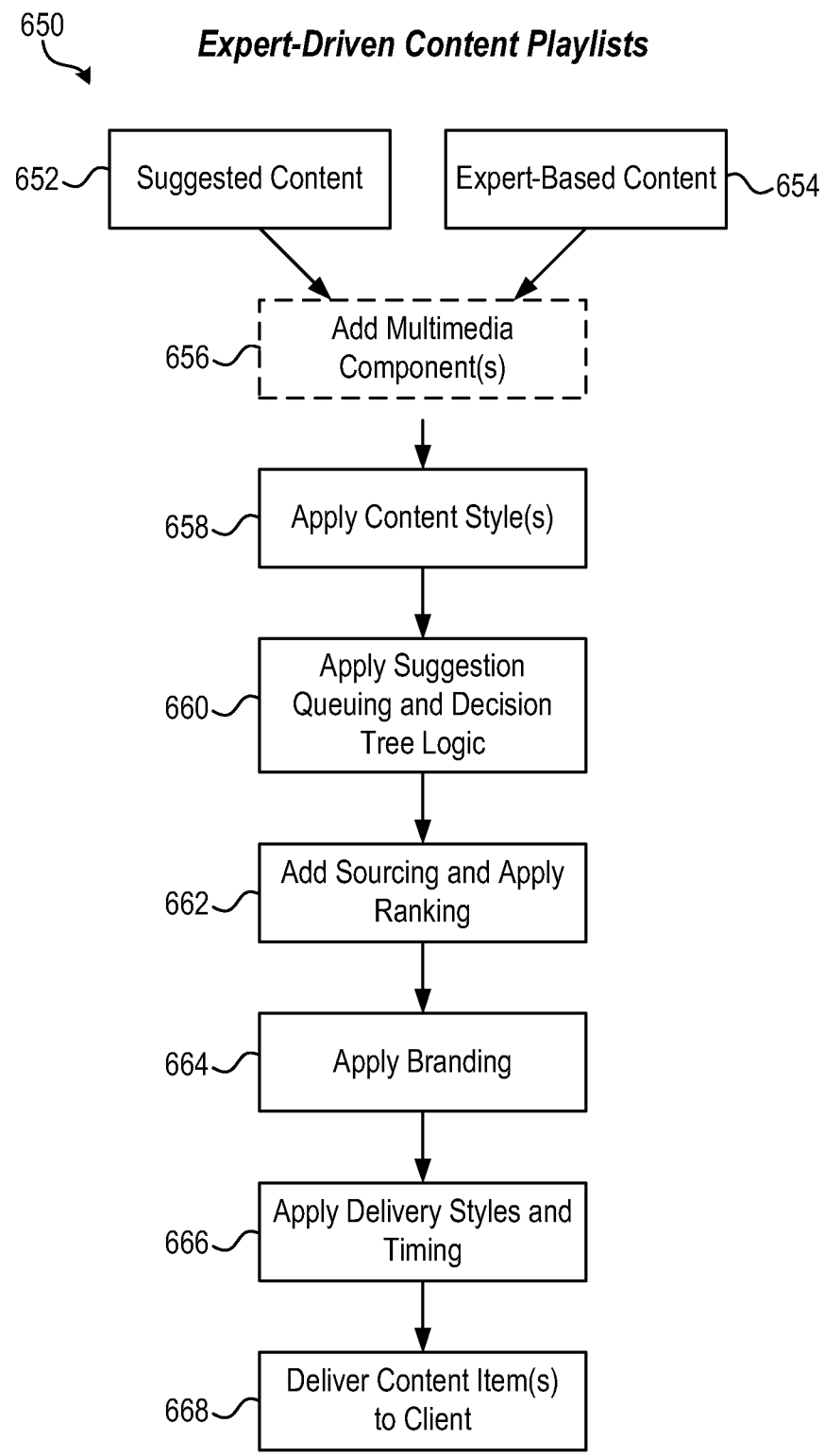
FIG. 6B illustrates data operations occurring in the generation and use of expert-driven content playlists according to an example described herein.

FIG. 6B provides an illustration of data operations 650 occurring in the generation and use of expert-driven content playlists in the information system 100 according to one example. The playlist may be created from one or a combination of suggested content 652 originating from the information system 100, or expert-based content 654 originating from the professional user (e.g., professional supporter 104A). The suggested content 652 may also include components of crowd-sourced content such as member-provided or group-provided content. The information system 100 may prompt, suggest, or encourage the generation of the expert-based content, and allow the expert to change portions of the suggested content.

Upon the definition of the content, the professional supporter may apply his or her coaching style through the use of templates and various tools. These include having the expert choosing to add multimedia components (operation 656). Suggestions may contain one or more of the following, for combination into a playlist for the member: Videos; Music (e.g., MP3) files; Picture files; Animated picture files; Coaching voiceover and integration to music libraries and services; Quotes; Event invitations; Textual Content; or External URL content.

The content may be refined further by applying one or more content styles (operation 658). The applied styles may include aspects of (or be chosen based on): profile types, geographic location, culture, or environment, as some example.

The content may be refined further by applying suggestion queuing and decision tree logic (operation 660). Such logic may provide the ability to: change a variable countdown timer used for delivery or use of content; change duration, difficulty, and frequency of suggestions (intensity); provide reminders, motivators, and prompts based on trigger logic; and maintain a content audit trail for verification.

The content may be refined further by applying sourcing and ranking (operation 662). The sourcing and ranking may provide the ability to add and cite information sources such as: clinical pathways; dietary programs; exercise regimes; or other affliction-specific content.

The content may be refined further by applying branding (operation 664). Branding capabilities provide the ability for a professional user to add: a logo; background signature sound; biography; listing of publications or books; or otherwise provide the ability to post specific content to users.

The delivery styles and timing of the content may also be changed or defined (operation 666). Professional users can use all feature controls of specific mobile devices (e.g., iOS versus Android, utilizing features such as speakers, sound, flash, vibrate) with the delivery of content. Other examples for use by a professional user may include: sending a SMS message in all-capitalized letters; vibrating the phone and using a camera flash; playing a soft noise such as a relaxing waves sound; playing a loud noise such as bowling pings crashing; changing phone wallpaper; making a call to supporter; or performing an automated follow up call to the client.

As a result of the preceding refinement operations, the items in the expert-driven content playlists may be delivered to the client 106 (operation 668). The professional user may be provided with additional controls and opportunities to further customize or shape the content, similar to the preceding operations.

Assessments and Motivation Workflow Examples

The information system 100 may offer mechanisms for clients to push or relay hardware monitoring data (e.g., physiological monitoring data) to professional users. For example, data from a client's personal exercise tracking device would be a complementary technology to the professional user's coaching, because it provides data points for a professional user to consider. The professional user seeing the exercise tracking device data might respond by saying: "I see you are not motivated in the morning. My suggestion is—first thing after you wake up, eat a banana, bagel, and do ten minutes of yoga. This will provide you with a boost of energy in the morning."

The information system 100 may enhance the data provided from the personal exercise device by leveraging a professional user's expertise to coach the client 106 to a better lifestyle. The data from the personal exercise device may also become an activity verification technology using GPS and timestamps. (For example, client A went for a walk around the block based on the recorded activity in the personal exercise device, and is beginning to perform more physical activity).

A client's use of an exercise tracking device does not change behavior by itself. But if a coach sees the data, holds the client accountable, and makes decisions on the data, then the exercise tracking device becomes an integrated part of the coaching plan from which the professional user can adapt his or her style to the particular client. Thus, professional users have an incentive for their clients to wear an exercise tracking device and use other data collection systems, because it can be used to enhance the service offerings and decision making with data points collected outside of in-person meetings.

Hardware monitoring and tracking devices may integrate directly or indirectly with interfaces and other services of the information system 100. Example types of hardware/software monitoring and tracking devices and applications include, but are not limited to: Nike+FuelBand; Nike+Running; Fitbit; My Fitness Pal; Jawbone UP; Map My Run/Ride; RunKeeper; DailyBurn; Weight Watchers.

The presentation and control of information from professional users from the information system 100 may be provided in connection with an internet-delivered graphical user interface, such as embodied in a website or software application. FIGS. 7A, 7B, 7C, 7D each provide examples of graphical user interfaces for interaction with the information system 100 in connection with the techniques described herein.

Figure 7A:
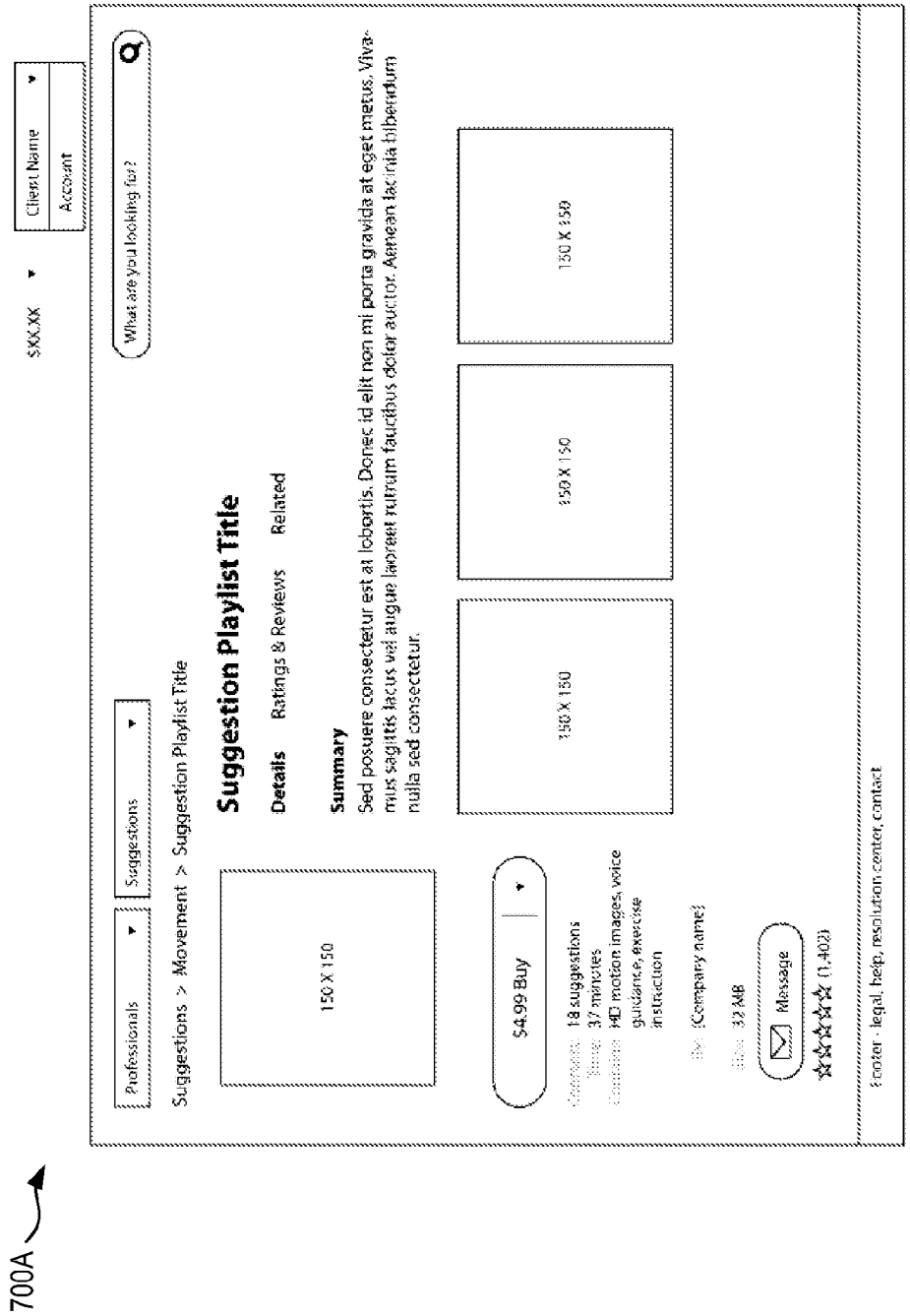
FIG. 7A illustrates a graphical user interface provided for displaying a content suggestion to a client in an expert-based content workflow according to an example described herein.

FIG. 7A depicts a graphical user interface 700A providing an illustration of a particular suggestion playlist, managed by a professional user, that may be purchased or subscribed to by the client 106. For example, a particular professional user may include a listing of exercise videos and suggestions, available for purchase or subscription. The interface may also provide links to further "details", "rating and reviews", and "related" suggestion playlists for the particular suggestion playlist.

Figure 7B:
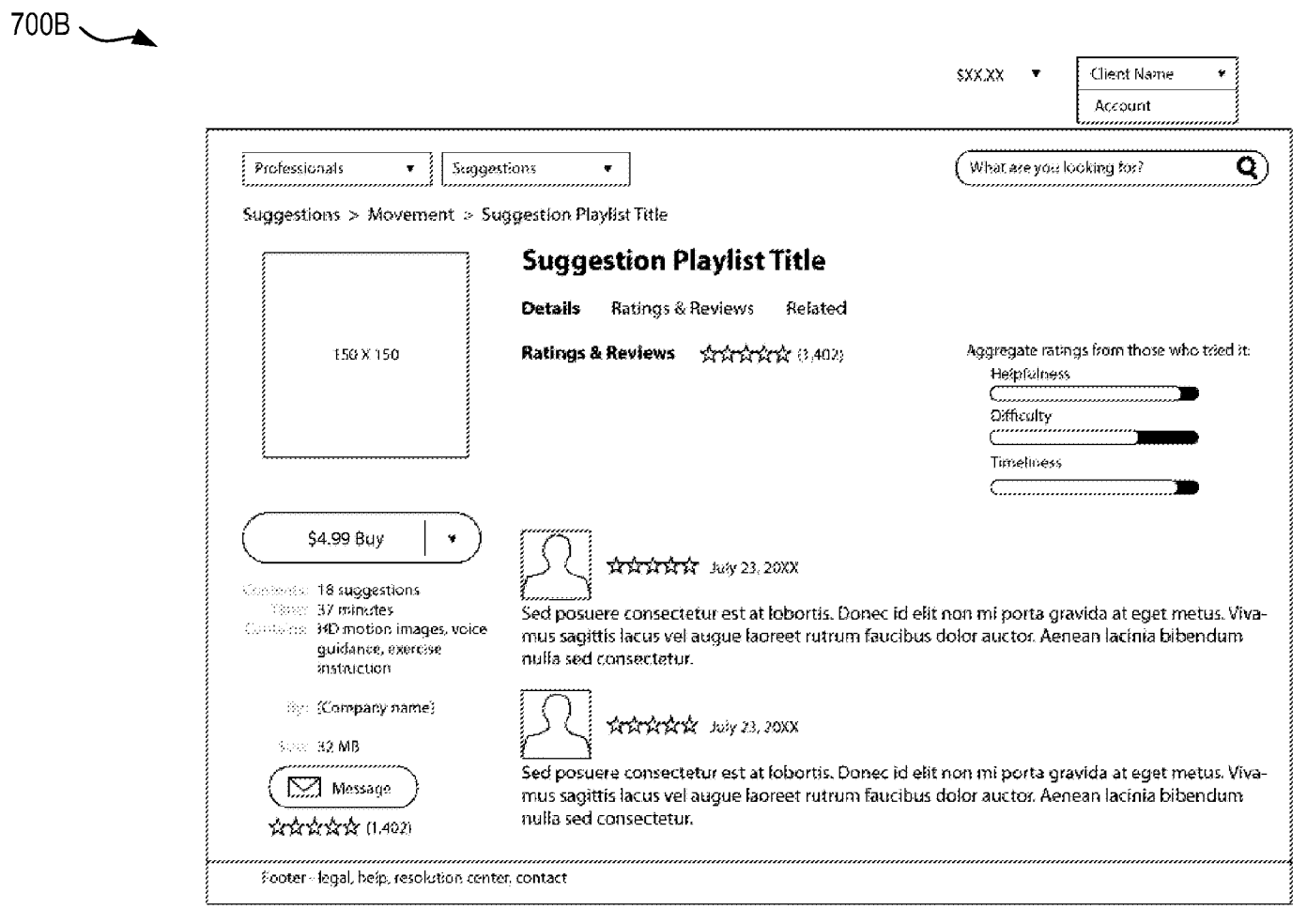

FIG. 7B depicts a graphical user interface 700B providing an illustration of reviews and ratings for a particular suggestion playlist, managed by a professional user, that may be purchased or subscribed to by the client. For example, different users may provide feedback and detailed reviews, including "helpfulness", "difficulty", and "timeliness" ratings for a particular professional user or playlist offered by a particular professional user.

Figure 7C:
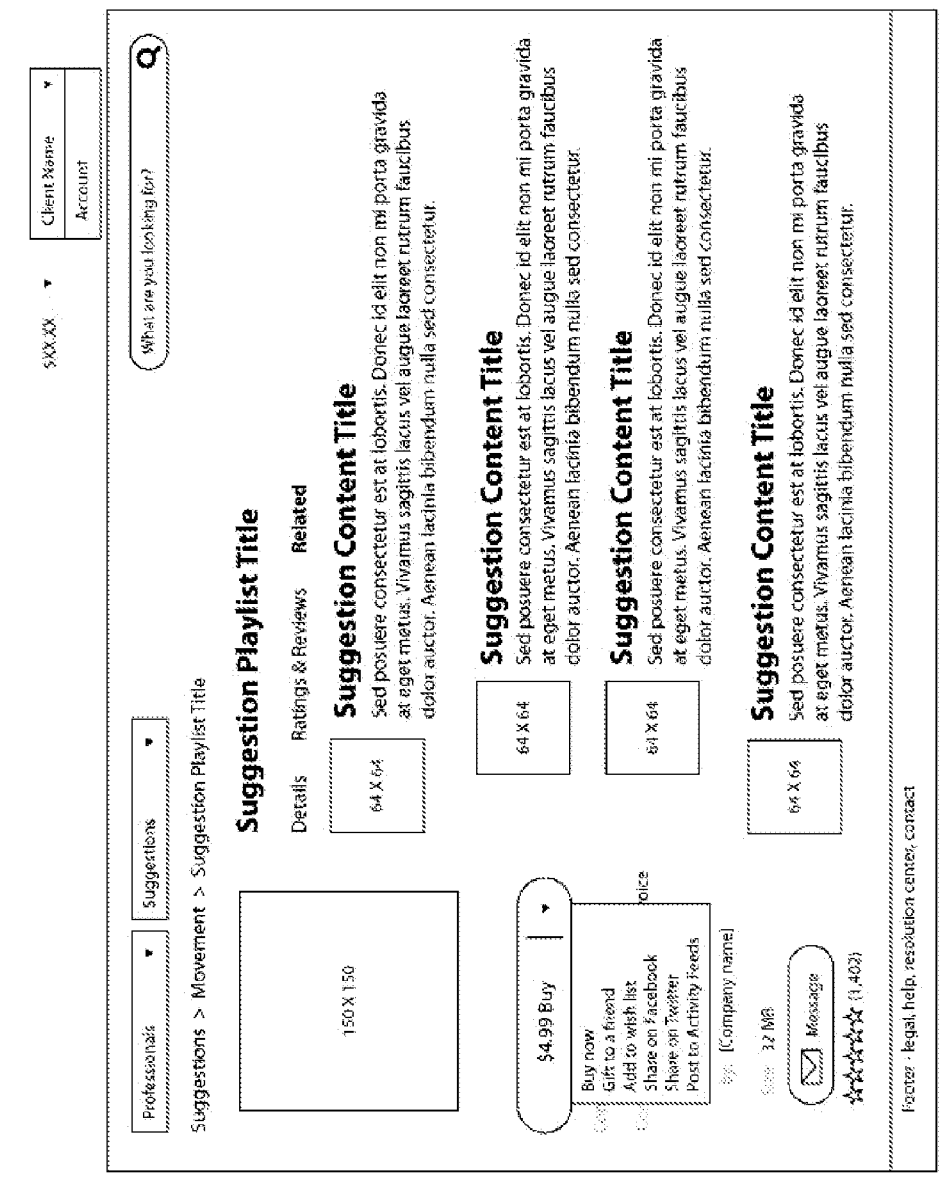
FIG. 7C illustrates a graphical user interface provided for displaying a content suggestion playlist of content suggestions in an expert-based content workflow according to an example described herein.

FIG. 7C depicts a graphical user interface 700C providing an illustration of related suggestion playlists, managed by professional users, that may be purchased or subscribed to by the client. This listing of related suggestion playlists may allow a particular client to browse available offerings by a particular professional user or based on a particular subject (such as "movement" activities). Other options in the interface may include enabling the client to buy or subscribe to the playlist; provide the playlist as a gift to a friend; add the playlist to a wish list; share to a social media site; or discuss within the activity feed managed by the information system 100.

Figure 7D:
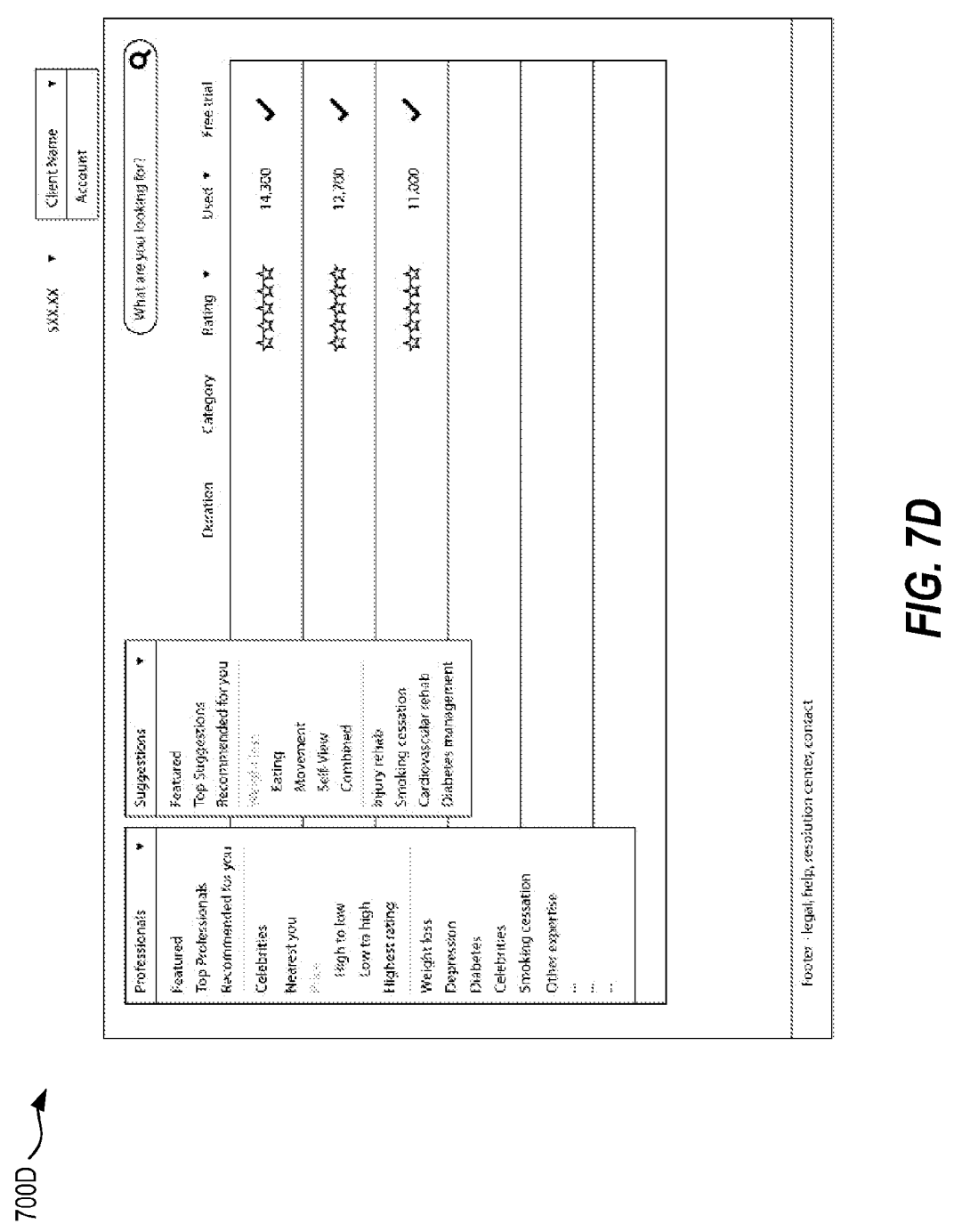

FIG. 7D depicts a graphical user interface 700D providing an illustration of menus to select offerings from professional users that may be purchased or subscribed to by the client. This may include the selection of categorizations for the client, including "featured" professionals, "top professionals", "recommended" professionals, "celebrity" professionals, location-nearest professionals, highest rated professionals, and offerings by price. The professionals may be selected based on a particular topic such as weight loss, depression, diabetes, smoking cessation, or other expertise. The available suggestions from particular professional users may be filtered by based on featured suggestions, top suggestions, recommended suggestions, categories such as injury rehab, smoking cessation, cardiovascular rehab, or diabetes management, and subcategories such as weight loss—eating, weight loss—movement, weight loss—self-view, or combinations of subcategories.

Figure 7E:
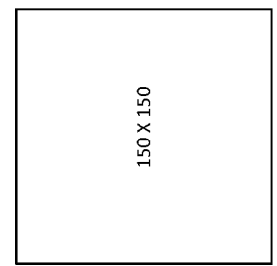
FIG. 7E illustrates a graphical user interface provided for displaying a content suggestion playlist having varying communication timings in an expert-based content workflow according to an example described herein.

FIG. 7E depicts a graphical user interface 700E providing an illustration of a suggestion playlists having varying communication timings. For example, the suggestion playlist may include the generation of suggestions and suggestion content at certain intervals (e.g., every 24 hours), for a certain duration (e.g., 15 minutes). Likewise, the timing of reminders, motivators, and number of times to repeat content or content delivery may also vary.

FIG. 7F depicts a graphical user interface 700F providing a specific interface to allow the change of suggestion timing for a suggestion playlist. For example, the timing of the content and associated content reminders and motivators may be customized by a coaching user, according to desired timing intervals, days of the week, or a repetition schedule.

Although the graphical user interfaces 700A-700F were provided with particular examples and illustrations, it will be understood that a wide variety of other graphical user interfaces may be used and employed in connection with the selection of professional user suggestions and the interaction with the goal-based workflows described herein.

Coaching and Communication Timing

The timing(s) of communications for a suggestion playlist of expert-driven content may vary depending on a number of variables. For example, these variables may include intensity (number of communications at a particular time); frequency (number of a communication); duration (how long a particular communication lasts); timing relevance (how well a particular communication maps to current member activity); delay (during what window a particular communication may be sent); multiple threads (sending two communications concurrently); or sequencing (sending one communication before another). Such communications may be delivered via chat, SMS, email, video chat, suggestions, prompts, motivators, reminders, tweets, social network messages, and the like.

Figure 8A:
FIG. 8A illustrates an example of variations of communication timing for communications from an expert in an expert-based content workflow according to an example described herein.
Figure 8A:

FIG. 8A depicts an example of variations of communication timing for communications from an expert in an expert-based content workflow within a chart 800. Different examples may be provided to map different intensities, sequences, frequency, and intensity, and multiple threads. Thus, particular communications 1-7 may be spaced and sequenced differently, providing a user with differing approaches to expert-driven suggestions.

Figure 8B:
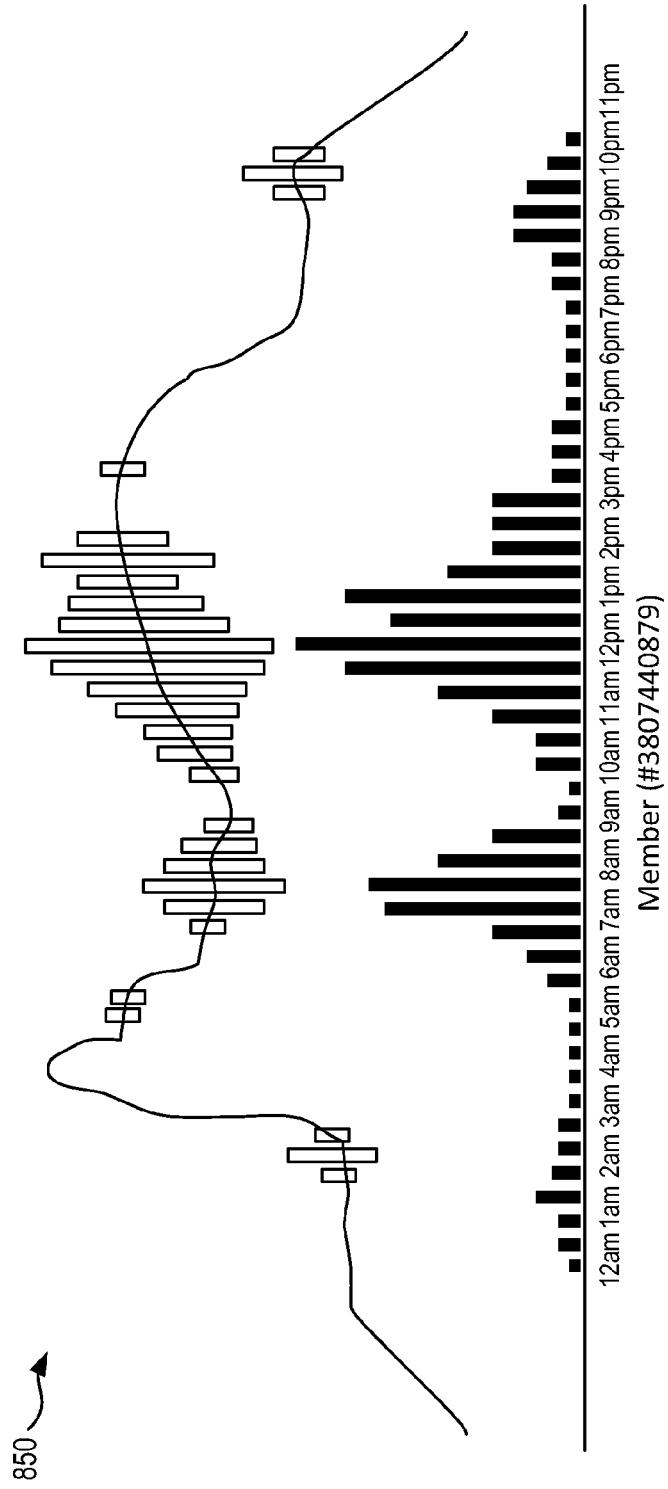
FIG. 8B illustrates an example illustration of communication timings mapped to user activity, profile information, and real time data elements in an expert-based content workflow according to an example described herein.

FIG. 8B depicts an example of variations of communication timings mapped to user activity, profile information, and real time data elements within a graph 850. As shown, a particular variable or combination of variables may correlate to responses and completed suggestions by category. The communication timings may be mapped to periods of time, based on responses and non-responses obtained over days, weeks, and months.

Dynamic Content-Driven Feedback and Prompts

The delivery, presentation, and response mechanisms for providing suggested content and suggested actions may be provided in a linear process to encourage action and appropriate feedback. As reinforcement to the playlists and the coaching style, a prompting system may be performed in connection with goal-based workflows managed by the professional users.

Prompt two-way communication initiated on conditional logic (e.g., from completion of a countdown timer, a count up timer, or an event trigger) may demand a response to an action, or serve as a one-way message for informational purposes (e.g., "We sent a message to your supporter to help you out"). Prompts may be configured to follow a "3 strike rule"—such that if there is no response to the first prompt, another prompt will be sent. If the client 106 does not respond to three messages (by notifications, email, texts) then the information system 100 will stop sending them.

One set of examples of prompted actions requiring a response may include: Suggestion expired; Need to fill out profile; Need to set destination; Need to add a Supporter; Subscription expired; Haven't participated in three days, and not on "vacation mode"; Low on integrity—Client may restart goal.

Prompts are an enhanced feature of coaching that push the client 106 towards his or her environmental goal 204 in a variety of styles (e.g. a mild, moderate, or aggressive style). Rather than simply monitoring the client's progress towards their environmental goal 204, the information system 100 may incorporate a pushing strategy with feedback, to obtain clarification of the various ways (and reasons) that the client 106 can be motivated towards his or her environmental goal 204.

The content suggestion engine techniques and operations described herein may also incorporate a variety of machine-learning and artificial intelligence concepts to adapt to context information (such as feedback), and deliver the content to the client 106 using appropriate timings and mechanisms. As the suggestion engine 102 produces suggested actions and obtains client feedback, the suggestion engine 102 may start to learn what is successful, and apply greater weights to a particular suggested action with a higher likelihood to succeed, thereby producing a cycle of improvement with a greater likelihood of progress towards goals 204.

Figure 9A:
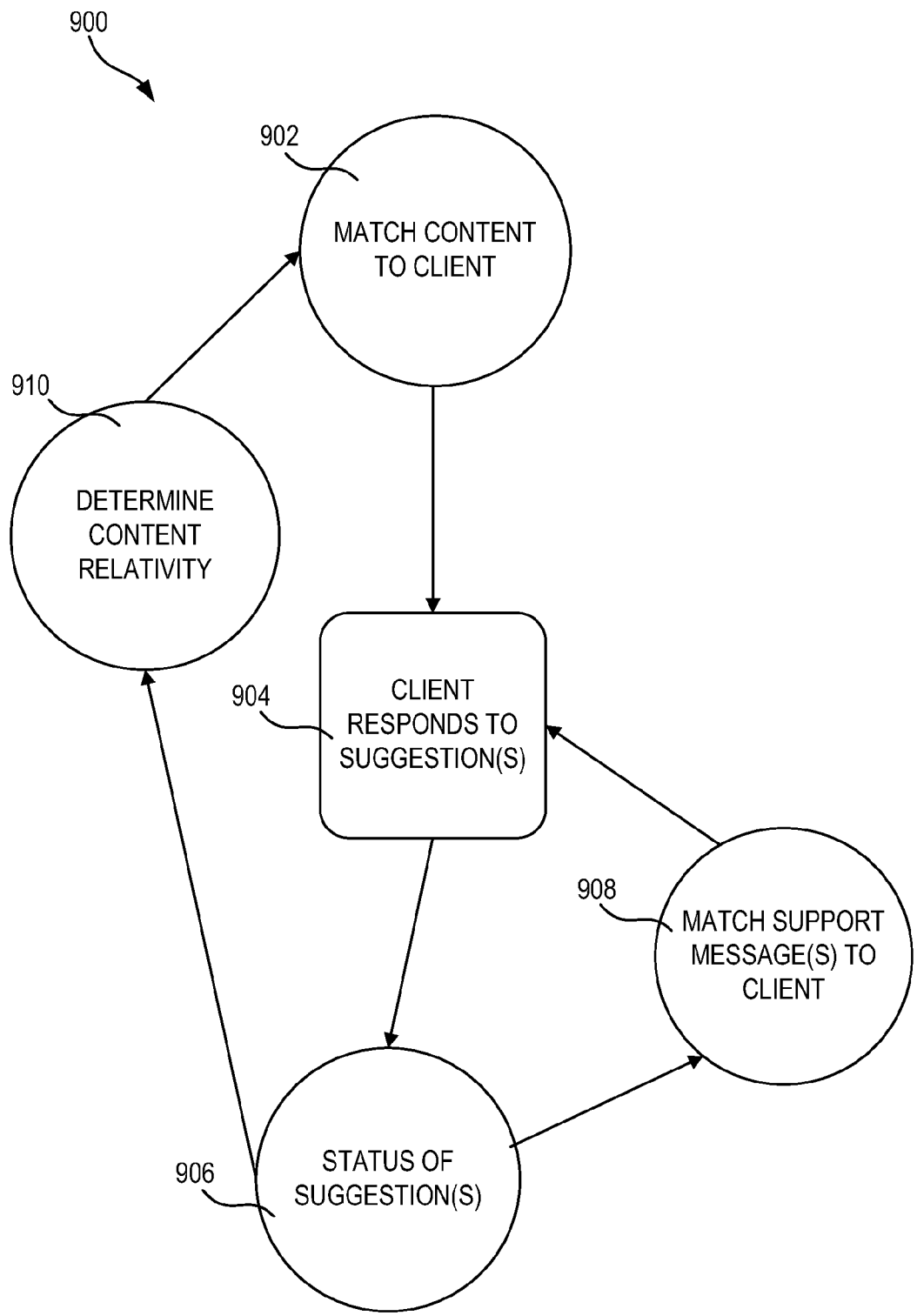
FIG. 9A illustrates an example technique of client interactivity with suggestions from an expert or a content suggestion engine in a content workflow according to an example described herein.

FIG. 9A illustrates an example technique 900 of client interactivity with a suggested action generated from the suggestion engine 102. At operation 902, content can be matched to a client 106, such as through data processing techniques, and filtering and weighting techniques produced in connection with a content suggestion or selection engine. At operation 904, the client 106 may respond to the suggested action, such as by accepting or rejecting the suggested action message. A lack of response within a period of time may also serve as a response. At operation 906, the status of the suggested action may be determined, such as determining if the suggested action message was accepted or rejected, or when the suggested action message is accepted and whether the action in the suggested action message is completed or not. At operation 908, a support message may be sent to the client 106, such as sending the client 106 an encouraging or motivating message to try to get the client 106 to complete the action. At operation 910, content relativity may be determined, and such relativity may be recorded for use in a future suggested action.

If questionnaires or psychological/physiological profiling indicate that a problem exists in an area (e.g., movement, eating, self view, etc.) that is different from the goal(s) 204 created by the client 106, then the system may ask the client 106 to review the goal(s) 204 or suggest the client 106 add another goal and indicate what that goal is. The system may also encourage the client 106 to achieve the goal 204 by giving reward points (e.g., kudos) or other incentives.

As a new client signs into the system and is given the opportunity to fill out questionnaires or to begin a suggested action, he or she may decide to use the system right away without filling out much information about them. These clients may be given a suggested action without much data about the client 106 that the suggestion engine 102 can process. A new client may also choose a program from a group of pre-created programs. These programs may include a suggested action that encourages the client 106 to achieve goal(s) 204 related to movement, eating, or self view, encourages the client to perform suggested actions that helps them learn the different features of the system, record how the client 106 uses the system, and suggests that the client 106 fill out questionnaires, at intervals or regularly. Getting feedback on a suggested action may help the suggestion engine 102 determine which suggested action to recommend to the client 106 after the program is complete.

When completed, a suggested action may be put back into a suggested action database. Any completed suggested actions may be withheld from retrieval from the suggested action database for a specified period of time. Such withholding time may be based on a client preference, such as the client 106 indicating that they prefer variety or sameness in the suggested action messages 502 that are presented to them. For example, if a client 106 indicates that they prefer variety, a completed suggested action may be withheld for a longer period of time than if the client 106 indicates they prefer sameness.

A goal may be accomplished when the client 106 indicates the goal has been accomplished or when the system determines that the goal has been accomplished. For example, the system may ask the client 106 or the client's supporters if the goal has been accomplished.

A client 106 may indicate that the suggested action was not timely. In such situations the system may ask the client 106 when the suggested action message would be or would have been timely. A timing tag related to a suggested action message may be adjusted accordingly. Timing tags may indicate an amount of time that the client 106 may be given to complete the task, such as 15, 30, 45, or 60 minutes, etc.

The difficulty rating (a tag) of a suggested action may be altered in accordance with client feedback. The weight of a suggested action may be altered as a client's ability to complete a type of suggested action changes. For example, if a client 106 rates a suggested action as too hard, the weight of the suggested action may be decreased and the weight of suggested actions with lower difficulty may be increased.

Figure 9B:
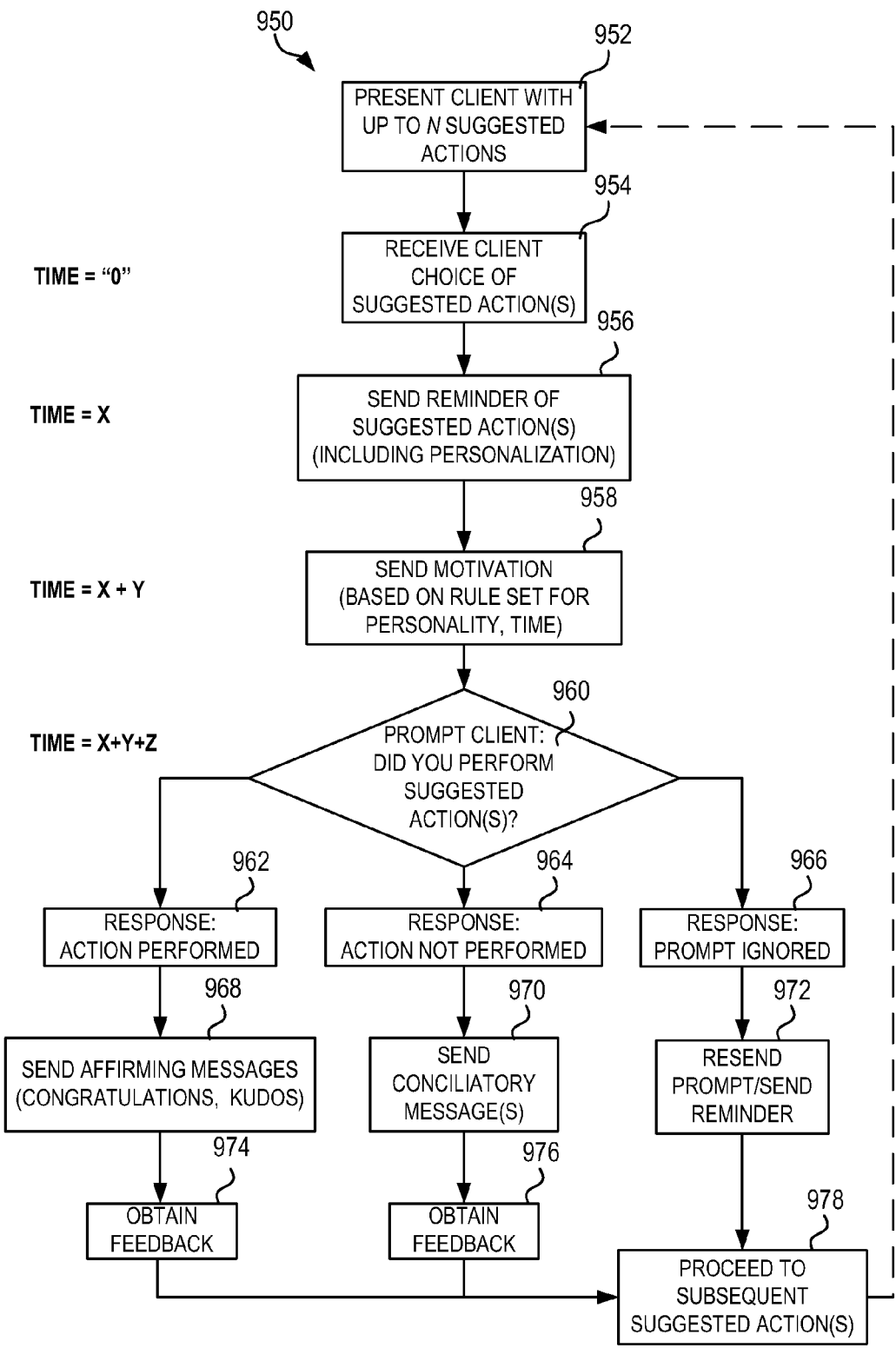
FIG. 9B illustrates an example technique of delivering suggested actions to and obtaining feedback from a client in a content workflow according to an example described herein.

FIG. 9B provides an illustration of a technique 950 for delivering suggested actions and obtaining feedback from human users according to an example. The delivery, presentation, and response mechanisms for providing suggested content and suggested actions may be provided in a linear process to encourage action and appropriate feedback.

At operation 952, a client 106 may be presented with up to N suggested actions. The suggested actions may be chosen from a pool of possible suggested actions using various data processing techniques, such as filtering and weighting. At operation 954, the system may receive the client's choice of suggested action(s). At operation 956, the system may send a reminder to the client 106 that the chosen suggested action should be accomplished. At operation 958, a motivating message may be sent to the client 106. The motivating message may be configured as a function of the client's personality type 210, the goal(s) 204, the time frame which the client 106 set to accomplish the goal 204, other data 208, or contextual user information.

At operation 960, the system may prompt the client 106 to indicate whether they performed the chosen suggested action or not. There are at least three responses the client 106 may provide.

In one scenario, at operation 962, the client 106 may respond that the suggested action was performed. At operation 968, the system may send an affirming message (e.g., a congratulations or kudos) to the client 106. At operation 974, the system may obtain feedback from the client 106, such as by asking the client 106 questions about their experience in performing the suggested action.

In another scenario, at operation 964, the client 106 may respond that the suggested action was not performed. At operation 970, a conciliatory message may be sent to the client 106 from the system. At operation 976, the system may obtain feedback from the client 106, such as by asking why the suggested action was not completed.

In another scenario, at operation 966, the client 106 may respond by ignoring the prompt. At operation 972, the system may resend the prompt, send a reminder that the suggested action should be performed, or present a different set of suggested actions, such as at operation 954. Regardless of the response received from the client 106, the system may proceed to present subsequent suggested actions at operation 978 (e.g., the process may start over at operation 952).

Figure 10:
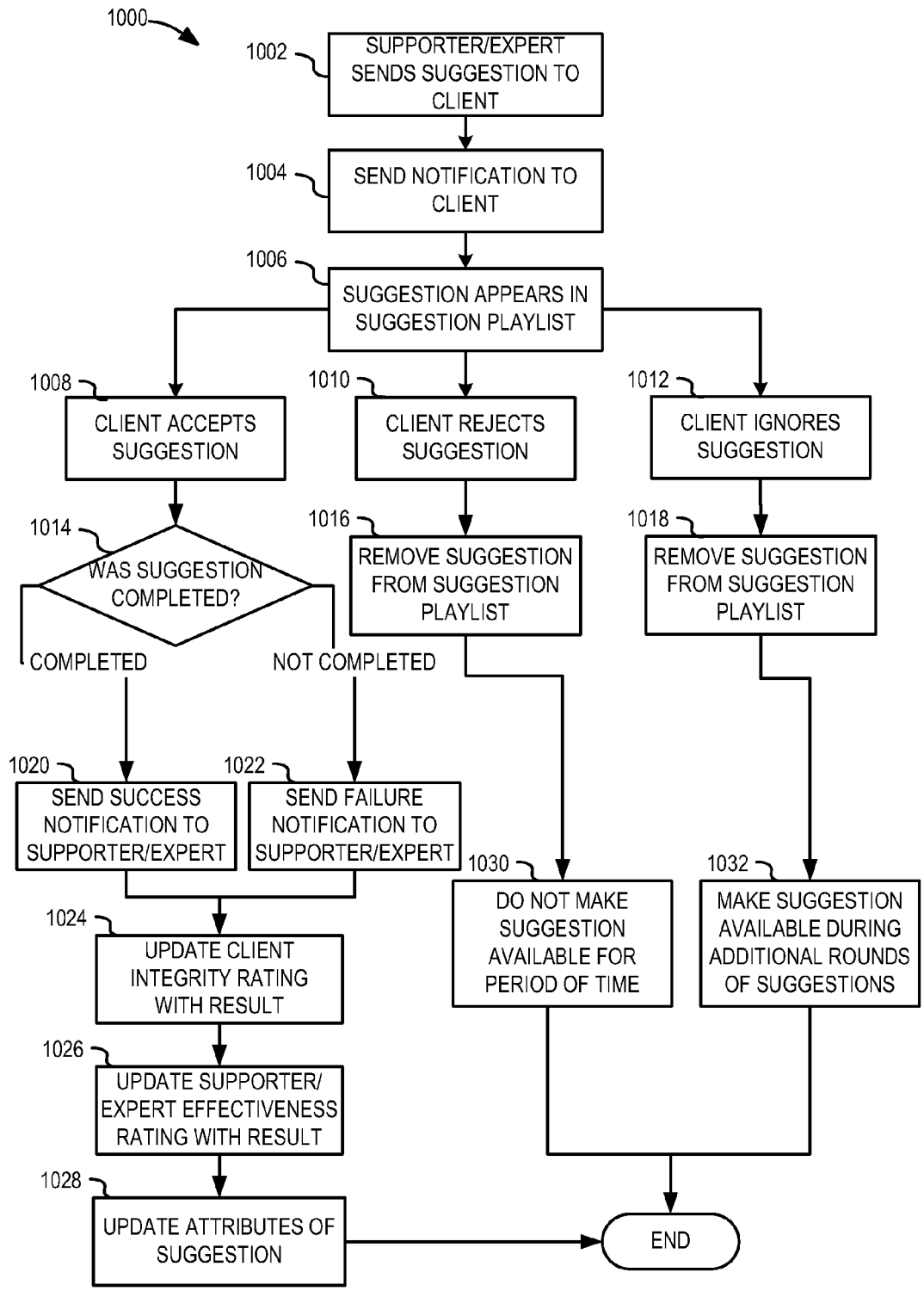
FIG. 10 illustrates an example technique of processing client interaction with suggested actions of a suggestion playlist in a content workflow according to an example described herein.

FIG. 10 illustrates an example technique 1000 of processing user interaction with suggested actions of a suggestion in a suggestion playlist in a goal-based workflow according to an example described herein. First, a supporter may send a particular suggestion to a client 106 (operation 1002). A notification of the particular suggestion may be sent to the client 106 (operation 1004). The notification may indicate that the suggestion has been sent to the client 106. The suggestion may appear in a suggestion playlist for the client 106 (operation 1006).

At this point the client 106 may take one of at least three actions: 1) the client 106 may accept the suggestion to make the suggestion part of the playlist (operation 1008); 2) the client 106 may reject the suggestion and refuse to perform the suggested action in the suggestion (operation 1010); or 3) the client 106 may ignore the suggestion and not do anything with regard to the suggestion (operation 1012).

If the client 106 accepts the suggestion, it may be determined if the suggestion was completed (decision 1014), such as by asking the client 106 if they completed the suggestion. If the suggestion was completed, then a success notification may be sent to the supporter who sent the suggestion (operation 1020). If the suggestion is not completed, then a reminder may be sent to the client 106 or a failure notification may be sent to the supporter who sent the suggestion (operation 1022). A client integrity rating may be updated in accord with the result (whether or not the client 106 completed the action) (operation 1024). A supporter effectiveness rating may be updated with the result (operation 1026). Various attributes (e.g., difficulty, helpfulness, timeliness) of the suggestion also may be updated (operation 1028).

If the client 106 rejects the suggestion (operation 1010), the suggestion may be removed from the suggestion playlist (operation 1016) and the system may prevent the suggestion from being suggested again for a period of time or indefinitely (operation 1030).

If the client 106 ignores the suggestion, the suggestion may be removed from the suggestion playlist (operation 1018) and the suggestion may be made available for the next, or a subsequent round, of suggestions (operation 1032), or the system may prevent the suggestion from being suggested again for a period of time.

A reminder may be provided to the client 106 regarding the suggestion. The reminder is a message from the information system 100 that is sent at a time between when a suggested action is accepted or ignored and when their suggested action is completed. A reminder can take the form of a calendar reminder. Reminders may be configured as a function of a category that the suggested action belongs to, such as eating, movement, or self view. In some examples, a self-view suggestion may be accompanied by a reminder to complete the action about 6 hours before the suggestion may be completed. In some examples, an eating suggestion may be accompanied by a reminder that is sent to the client 106 about a half-hour before the meal or preparation for the meal. In some examples, a movement suggestion may be accompanied by a reminder that is sent to the client 106 about 12 hours before the client 106 is to complete the suggestion. Other notifications may be sent to the client 106 or other users of the application. A notification may be a "call to action" that directly impacts the client 106, a supporter in the supporter network 104, or a dual role user regarding their support network, progress, account settings, subscription, or other miscellaneous items.

Figure 11:
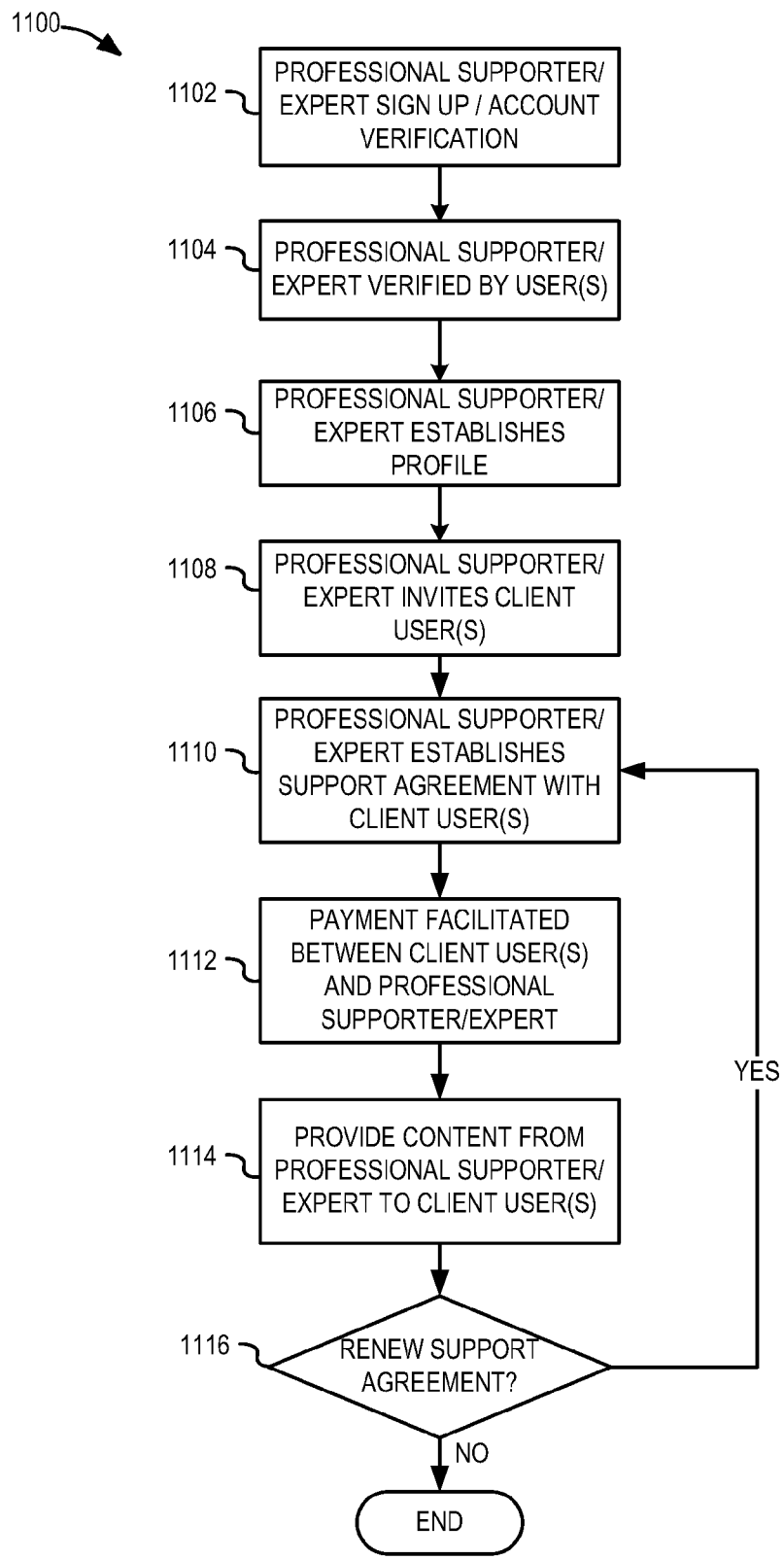
FIG. 11 illustrates an example technique of establishing a support agreement between a professional supporter and a client according to an example described herein.

In some examples, the supporter may be a "professional supporter," such as a professional user as described herein, and designated to provide fee-based or compensated support to various clients. FIG. 11 depicts an establishment of a support agreement with between client users and a professional supporter, in an example technique 1100 according to an example described herein.

As shown, a professional supporter may establish an account through a sign up and account verification process (operation 1102). This may include the professional supporter filling out a sign up form, and be subject to an account verification or confirmation process. The professional supporter then may be verified by one or more users (operation 1104), which may include administrative users, or recommendations from clients. For example, the professional supporter may be a "basic" or regular supporter until verified/confirmed. The professional supporter will then establish their profile (operation 1106) to include information such as area of practice/expertise, certification(s), qualifying degree, billing for services, biographical information, publications, client reviews, and contact information.

As shown, the professional supporter may invite one or more client users (operation 1108) or otherwise select certain clients for a supporting role. For example, invitations may be sent by email, social network, or based on client actions. After the respective clients accept the supporting role, the professional supporter will establish a support agreement with the one or more client users (operation 1110). This support agreement may include varying levels of support based on varying fee levels and charges. In some examples, the client user may also suggest changes to the support agreement for approval by the professional supporter.

After establishment of the support agreement, payment is facilitated between the one or more client users and the professional supporter (operation 1112). This payment may occur before, during, or after the term of the support agreement. The subscription system may take a portion of the payment (for example, compensating the professional supporter 70% of all payments received). During the support agreement, the professional supporter will provide content (including customized content) to the one or more client users (operation 1114). In some examples, the professional supporters may receive more status information about the psychological or activity status of one or more client users than basic supporters. Also in some examples, the support agreement may be renewed (decision 1116), which if renewed, will result in a new support agreement (operation 1110), payment (operation 1112), and content to the client (operation 1114).

Supporter Interaction and Workflow Examples

The goal-based workflows may be configured to integrate selection and delivery of suggested content with insight and input from supporters in the supporter network 104. A supporter may be a personal acquaintance of a client, a trained motivator, a dietary professional, a psychologist or other psychological expert, another client facing a similar problem, a random person interested in helping people achieve their goals, or any other person the client 106 may choose to help them achieve their goals. For example, a client may know that they need someone to "be on their case" about completing suggestions and may know somebody who is good at motivating them to complete actions. That person could be a supporter for that client. In another example, a client having trouble eating can have a supporter who is a dietary expert with experience in nutrition and curbing bad eating habits. The supporters may be chosen by the client 106 or assigned to the client 106 by the system. Another user of the application may request to be a supporter for the client 106 and the client 106 may be given an opportunity to either accept or reject the request.

Figure 12A:
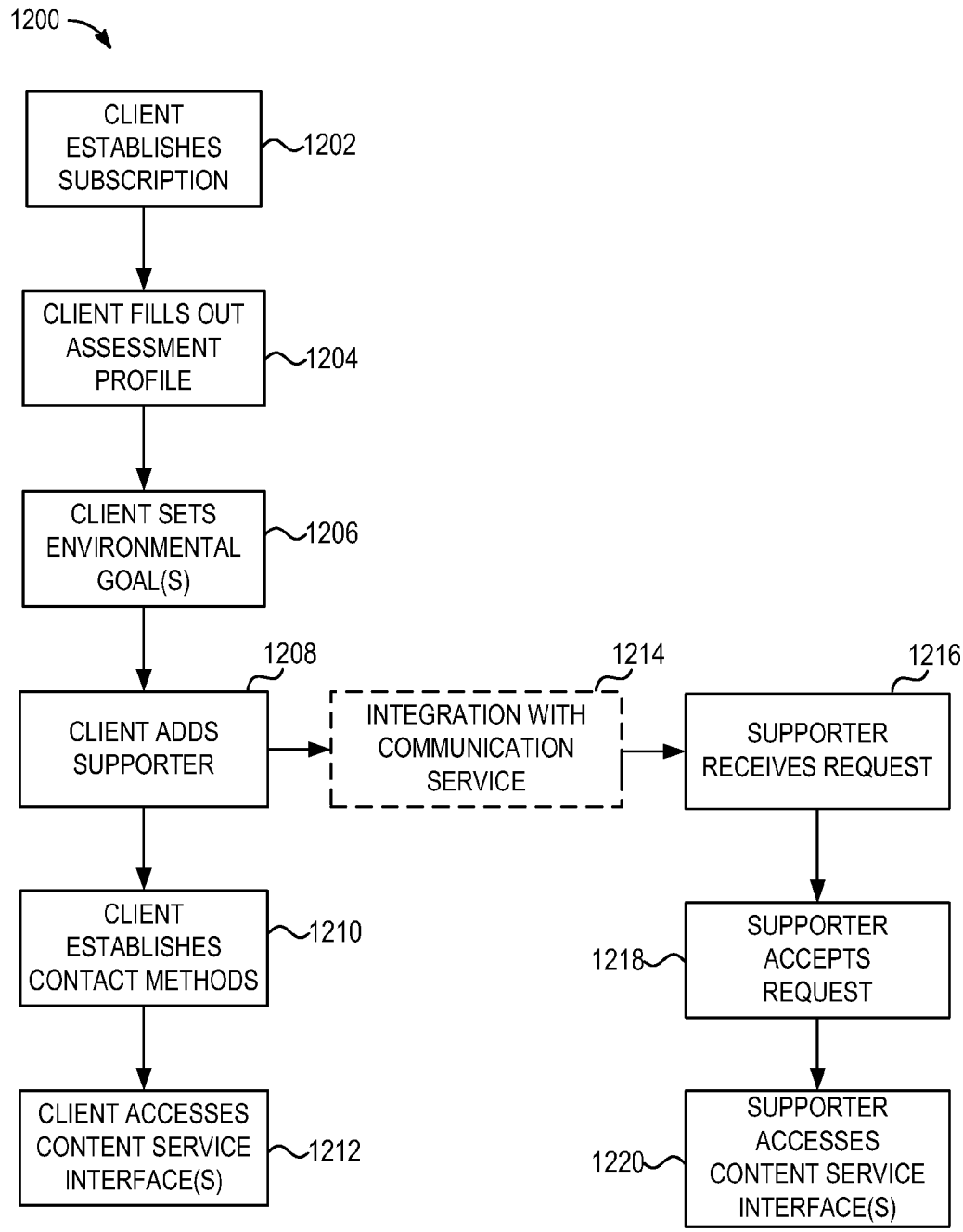
FIG. 12A illustrates a flowchart depicting a workflow for client and supporter interaction in connection with a client content service interface according to an example described herein.

FIG. 12A illustrates a flowchart depicting a workflow 1200 for client and supporter interaction within an information service providing a software or other user-interactive application for clients and supporters. A client may establish a subscription to the application (operation 1202). This may be accomplished by visiting a website or purchasing/downloading software and following steps suggested by the website or software. The client 106 can fill out an assessment profile (operation 1204). The assessment profile may be configured to obtain data 208 from the client 106. The client can set one or more goals (operation 1206). The client can choose supporters, supporters may be recommended to the client 106, supporters may request to work with the client 106, or supporters may be otherwise associated with the client 106 (operation 1208). The client 106 also establishes methods of which they would prefer to be contacted by supporters or the application (operation 1210). The client 106 can access the client content service interface of the application (operation 1212) (e.g., a client content service interface shown in FIG. 13).

When the client 106 adds a supporter (operation 1208), a request may be sent to the supporter. Optionally, this may be accomplished through interaction with the communication interface (operation 1214) (e.g., a communication interface shown in FIG. 13). The supporter may receive the request (operation 1216). Using the application, the supporter may accept the request to become a supporter for the client 106 (operation 1218). The supporter may access the supporter content service interface of the application (e.g., a supporter content service interface shown in FIG. 13) (operation 1220).

Figure 12B:
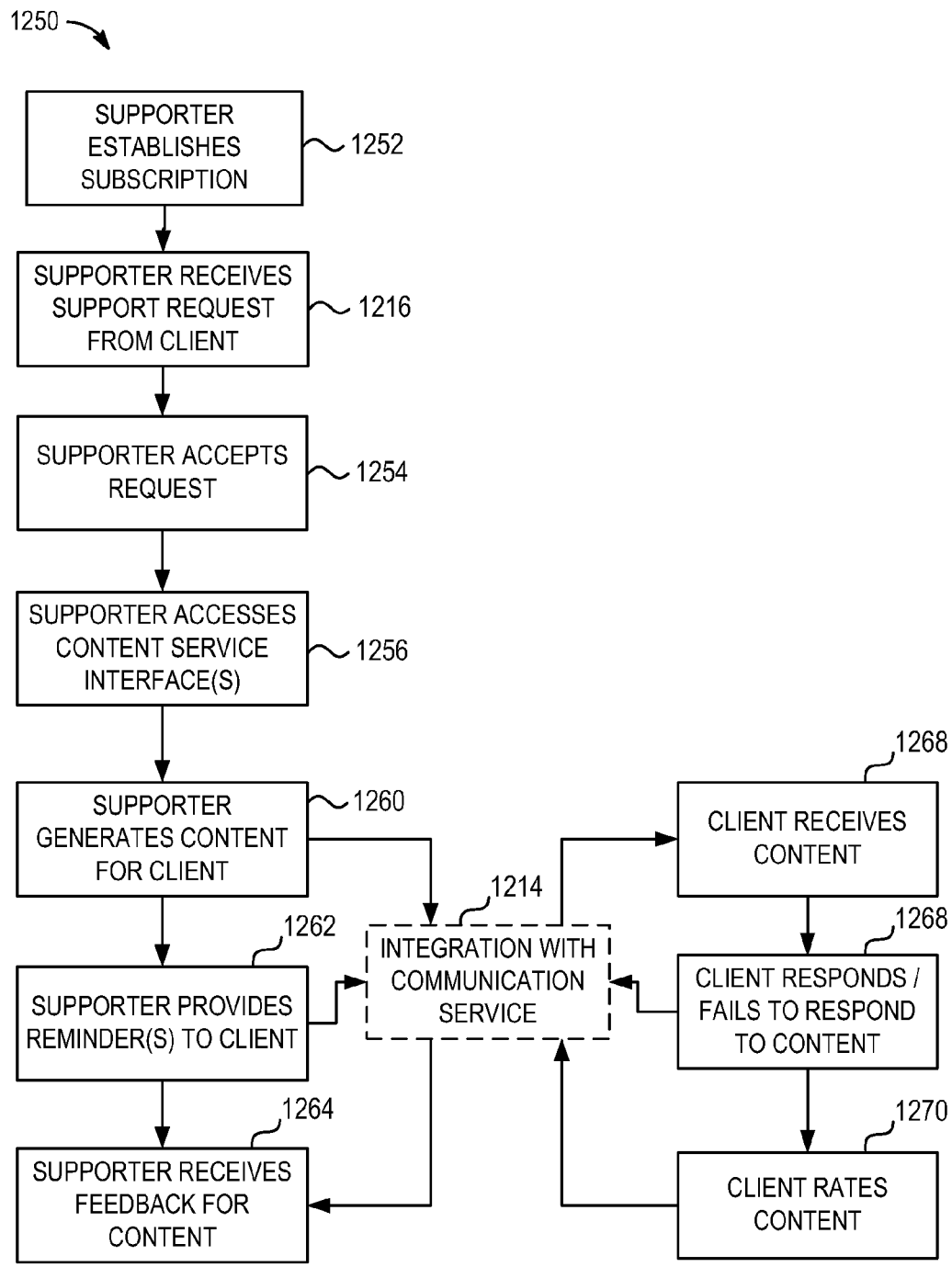
FIG. 12B illustrates a flowchart depicting a workflow for client and supporter interaction in connection with a supporter content service interface according to an example described herein.

FIG. 12B illustrates a flowchart depicting a workflow 1250 for supporter interaction within an information service providing a software or other user-interactive application for clients and supporters. In correspondence with the configuration of FIG. 12A, the flowchart illustrates supporter-based operations to establish a subscription and generate content for communication to supported clients.

In the workflow 1250, a supporter may establish a subscription to the application (operation 1252). This may be accomplished by visiting a website or purchasing/downloading software and following steps suggested by the website or software. The supporter will receive the support request from a client (operation 1216). In response, the supporter will accept the request (operation 1254). The supporter then accesses the content service interface(s) (operation 1256), and uses the interface to generate content for the client (operation 1260). The content is then provided to the client through integration with the communication service (operation 1214).

In connection with the mechanisms provided by the integration with the communication service (operation 1214), the client may receive content from the supporter (operation 1268), and provide a response (or fail to provide a response) to the content (operation 1268). To encourage response to content, the supporter may provide one or more reminders to the client regarding the content and associated actions or goals (operation 1262). The client may also provide a rating of the content (operation 1270). The rating of the content, and appropriate reminders and feedback (operation 1264), may be exchanged through the integration with the communication service (operation 1214).

The supporter may be provided with feedback on a variety of environmental data values of the client, provided in context to transmit meaningful data about the client to the supporter. The environmental data values may include moment-in-time data used to craft informed and relevant selections, including environmental considerations, psychological or physiological considerations, even the weather at the location of the user. Further, the supporter may be able to choose suggested content among available choices and provide guidance to the communication process (such as choosing one option among three suitable options, based on the supporter's understanding of which suggested content is most relevant or would be most well-received by the client).

Figure 13:
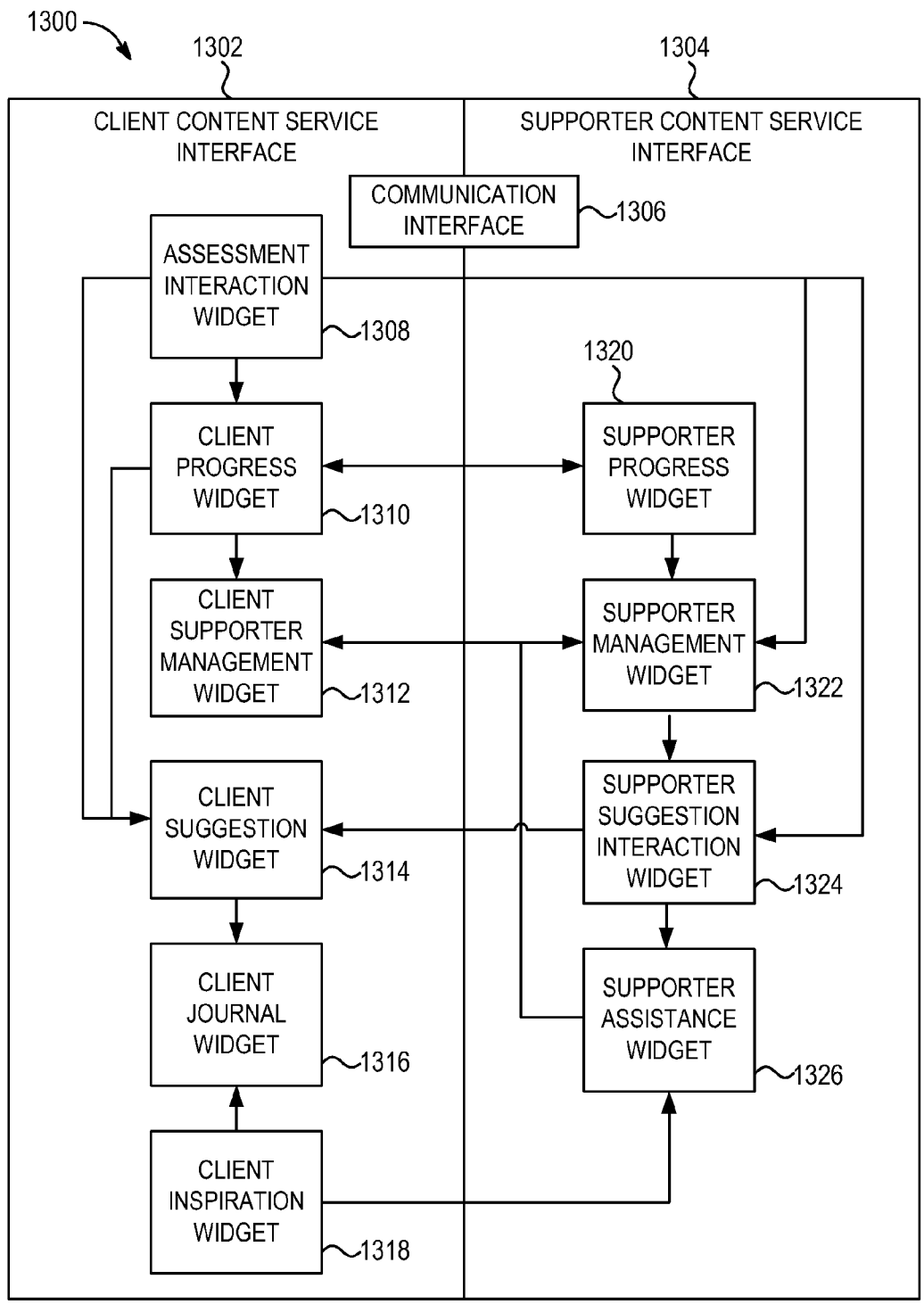
FIG. 13 illustrates a block diagram of interface components for client and supporter interaction within a content service according to an example described herein.

FIG. 13 illustrates a block diagram of interface components 1300 for client and supporter interaction (e.g., a professional user coaching interaction with a particular client) within a content service according to an example described herein. The interface components 1300 may include a client content service interface 1302, a supporter content service interface 1304, or a communication interface 1306 between the client content service interface 1302 and the supporter content service interface 1304.

The client content service interface 1302 may include an assessment interaction widget 1308, a client progress widget 1310, a client supporter management widget 1312, a client suggestion widget 1314, a client journal widget 1316, or a client inspiration widget 1318. The assessment interaction widget 1308 may be communicatively coupled to the client suggestion widget 1314 or the client progress widget 1310. The assessment interaction widget 1308 may be communicatively coupled to the supporter content service interface 1304, such as to a supporter management widget or a supporter suggestion interaction widget 1324 of the supporter content service interface 1304. The assessment interaction widget 1308 may determine an amount of client involvement with the application and may cater the presentation of the suggestions and other messages based on the amount of client involvement.

The client progress widget 1310 may be communicatively coupled to the client supporter management widget 1312 or the client suggestion widget 1314. The client progress widget 1310 may be communicatively coupled to a supporter progress widget 1320 of the supporter content service interface 1304. The client progress widget 1310 may monitor a client's progress towards a goal. The client progress widget 1310 may send other widgets updates regarding the client's progress towards a goal, such as indicating when a suggestion is completed or how many suggestions the client 106 has left to complete before the goal is accomplished.

The client supporter management widget 1312 may be communicatively coupled to a supporter management widget 1322 or a supporter assistance widget 1326 of the supporter content service interface 1304. The client supporter management widget 1322 may be configured to prompt a client for data 208, feedback on the client's opinion of the system, and may send information to the supporter management widget 1322, such as information indicating to the supporter management widget 1322 that a supporter should send a suggestion to the client 106 or that the supporter should send an encouraging message to the client 106.

The client suggestion widget 1314 may be communicatively coupled to a supporter suggestion interaction widget 1324 of the supporter content service interface 1304. The client suggestion widget 1314 may present suggestions to the client 106, which the client 106 may then accept, reject, or ignore. The suggestions presented may be received from the supporter suggestion interaction widget 1324 or content suggestion engine.

The client journal widget 1316 may be communicatively coupled to the client inspiration widget 1318. The client journal widget 1316 may allow the client to have a sort of diary that records their experience(s) interacting with the application. The client journal widget 1316 may prompt the client for entries or may be passive and allow the client to create journal entries as the client desires.

The client inspiration widget 1318 may be communicatively coupled to the supporter assistance widget 1326. The client inspiration widget 1318 may record the reasons that the client 106 is trying to achieve a goal and remind the client 106 about those reasons. The reminders may be random, scheduled, or configured to not appear in some instances, such as when a client indicates that they do not want to receive these reminders.

The supporter content service interface 1304 may include the supporter progress widget 1320, the supporter management widget 1322, the supporter suggestion interaction widget 1324, or the supporter assistance widget 1326. The supporter progress widget 1320 may be communicatively coupled to the supporter management widget 1322. The supporter progress widget 1320 can keep a supporter abreast of how the client 106 is progressing towards the goal.

The supporter management widget 1322 may be communicatively coupled to the supporter suggestion interaction widget 1324. The supporter management widget 1322 may monitor how the supporter interacts with the client 106 and determine whether or not that interaction is effective. These determinations may be sent to the supporter suggestion interaction widget 1324.

The supporter suggestion interaction widget 1324 may be communicatively coupled to the supporter assistance widget 1326. The supporter suggestion interaction widget 1324 may prompt a supporter to send a suggestion, encouraging message, or other content, such as scientific articles or inspirational stories, to the client 106. The supporter suggestion interaction widget 1324 may indicate to the supporter that the supporter should leave the client 106 alone for a specified amount of time (e.g., minutes, hours, days, weeks, etc.).

The supporter assistance widget 1326 may help the supporter choose suggestions, personalize suggestions, or draft other messages to the client 106. The supporter assistance widget 1326 may help the supporter navigate the application or get in contact with other supporters, such as other supporters helping clients with similar goals or lifestyles.

The types and amount of communications between the various widgets (and between the client and supporter) may be customized, to be expanded or narrowed with user preferences. For example, various privacy settings and preferences may be set by a user to share more or less information about specific activities or conditions, or to send and receive more or less information from particular users. Many of the data points can be customized to different levels to control the types and amount of interactions.

Figure 14:
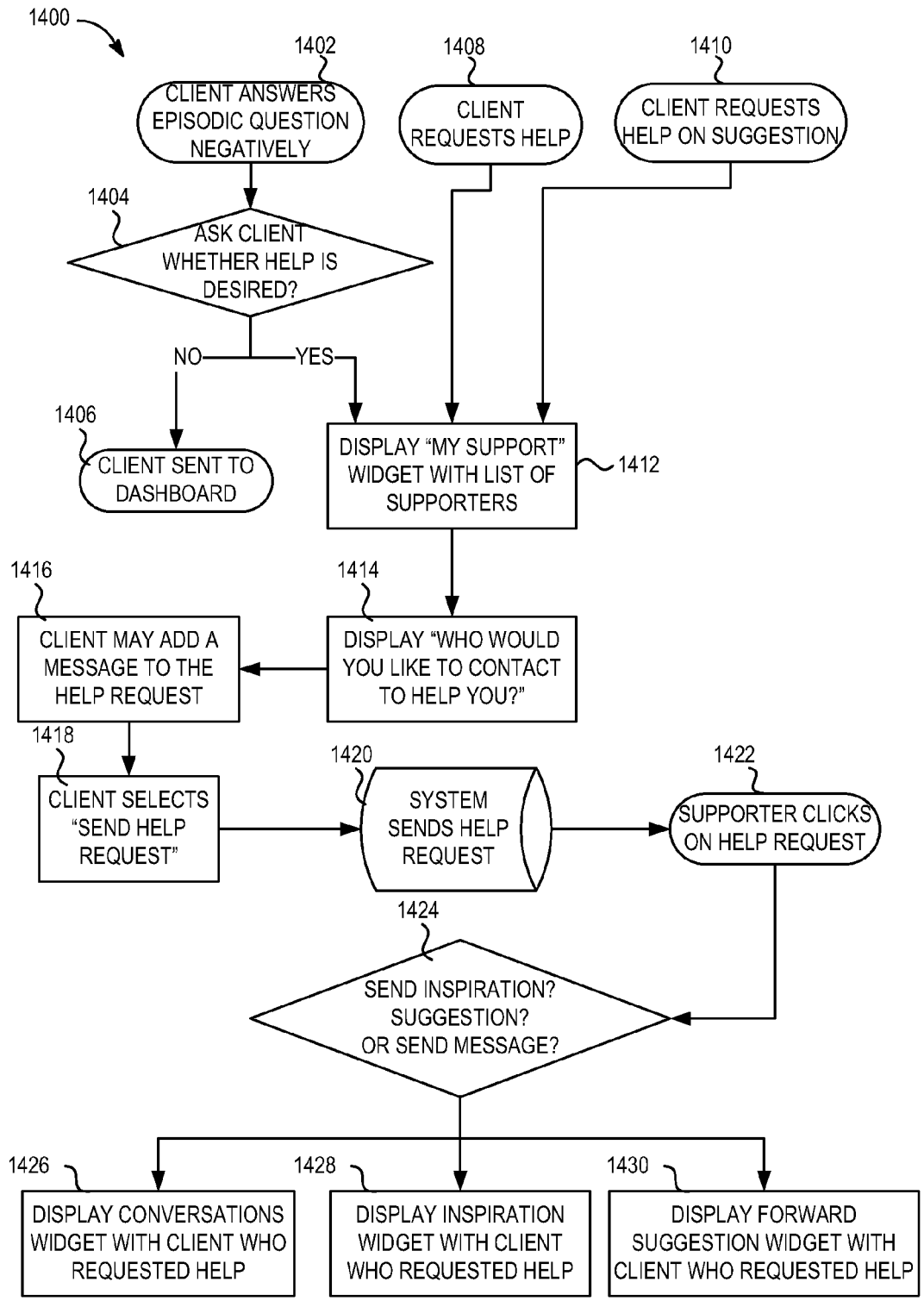
FIG. 14 illustrates a flowchart of interaction between a client and a supporter in a content workflow according to an example described herein.

FIG. 14 illustrates a flowchart 1400 of supporter interaction (e.g., professional user interaction) with a client in a goal-based workflow according to an example described herein. When a client answers an episodic question (e.g., a question to the client 106 that is designed to obtain or measure the psychological state of the client 106) negatively, such as by responding "terrible", "not good", or the like to an episodic question "How are you today?" (operation 1402), the application can ask the client 106 if they would like help (operation 1404). When the client 106 indicates that they do not want help, the client 106 can be sent to the dashboard (operation 1406) (further described below with reference to dashboard 1570 in FIG. 15B).

When the client 106 indicates that they do want help, such as by answering "Yes" to the question "would you like help?" (operation 1408), requesting help using the client supporter management widget 1312, or requesting help on a link provided on a suggestion (operation 1410), then the client 106 may be presented with a list of supporters. The list of supporters may be provided from list of supporters from the client supporter management widget 1312 (operation 1412). The client 106 may be asked who they would like to contact to help them (operation 1414). When the client 106 requests help using a link or button on a suggestion, such as an accepted suggestion, that was sent to the client 106 from a supporter, then the client 106 may be directed (e.g., automatically), to the supporter that sent the suggestion. The client 106 may select one or more supporters, or groups of supporters to help. The client 106 may add a message to a help request (operation 1416) and the help request may be sent to the respective supporter(s), such as by the client 106 selecting a "send request" option (operation 1418). The application may send the help request (along with any messages the client 106 added) to the selected supporters (operation 1420). The help request may be accompanied by notifications that are configured to alert the supporter, such as a text, email, or other notification, that the client 106 is looking for help.

The supporter can click on or otherwise interact with the help request (operation 1422). The application may prompt the supporter to take an action (decision 1424) by asking if the supporter if he or she would like to send an inspirational message, suggestion, other message, or if they would like to contact the client 106 directly. If the supporter would like to contact the client 106 directly then a conversation box or other conversations widget can be opened for the supporter to chat with the client 106 (operation 1426). If the supporter would like to send inspiration to the client 106, the client inspiration widget 1318 may be accessed so that the supporter can determine what inspires the client 106 (operation 1428). If the supporter would like to forward a suggestion produced by the information system, a supporter suggestion interaction widget 1324 or other suggestion forwarding widget may be accessed to forward suggestions from the supporter to the client 106 (operation 1430).

Figure 15:
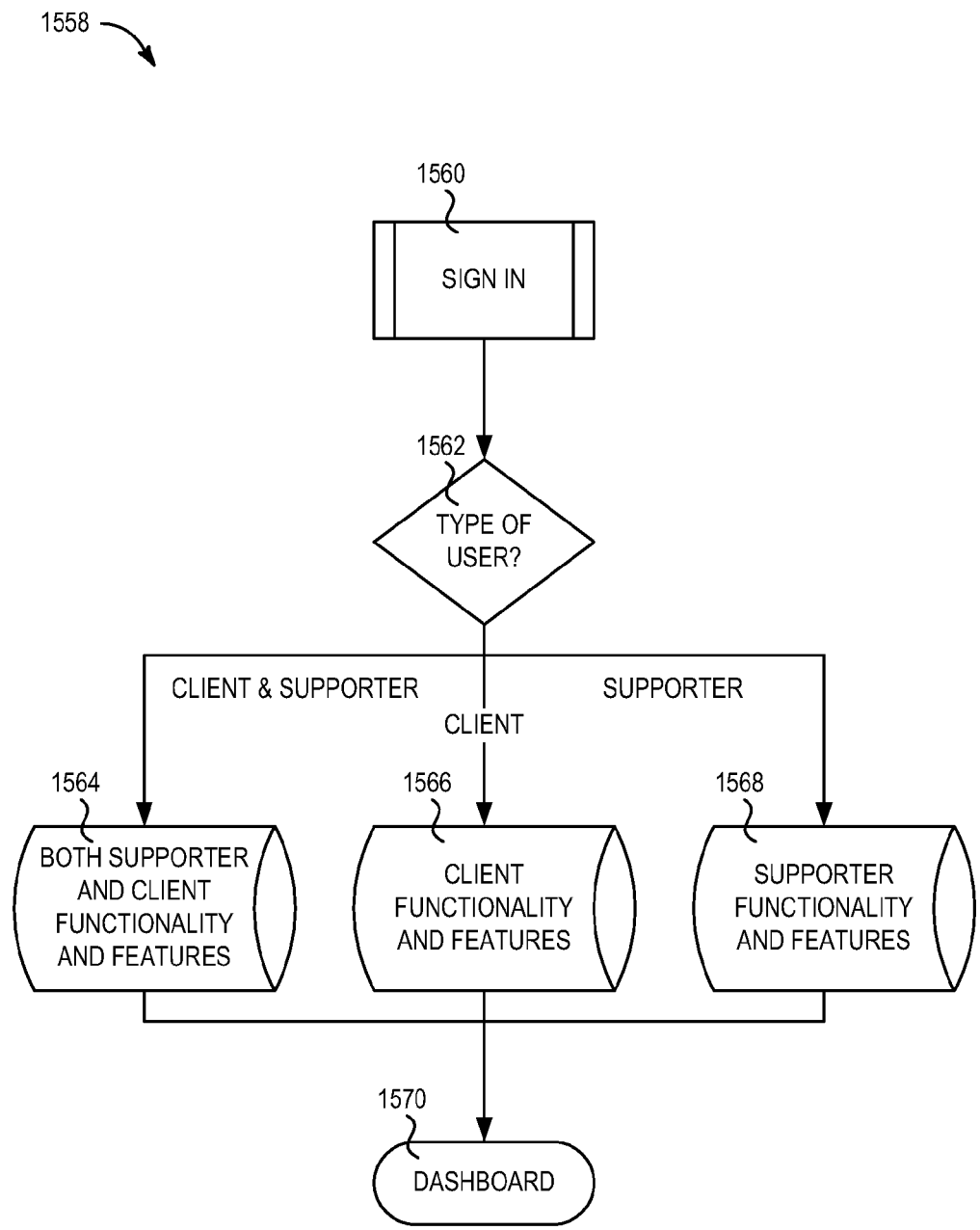
FIG. 15 illustrates a flowchart of data functionality and feature components available to a client and a supporter within an information service according to an example described herein.

FIG. 15 illustrates a flowchart 1558 of data functionality and feature components available within an information service according to an example described herein. A client or supporter may access the functionality and feature components through sign in to the information service (data operation 1560). The type of user that has signed in can be determined (decision 1562). If the user is both a client and a supporter, the supporter and client functionality and features may be loaded for viewing and interaction (using data set 1564). If the user is just a client, then the client functionality and features may be loaded for viewing and interaction (using data set 1566). If the user is just a supporter, then the supporter functionality and features may be loaded for viewing and interaction (using data set 1568). Client functionality and features (from data set 1566) may include the widgets provided in the client content service interface 1302 (described with reference to FIG. 13). Supporter features and functionality (from data set 1568) may include the features and functionality of the widgets provided in the content service interfaces 1302, 1304. A dashboard 1570 that displays the client or supporter features and provides the client or supporter functionality to the respective user may be displayed to the user.

Computing System Architectures and Example Implementations

Figure 16:
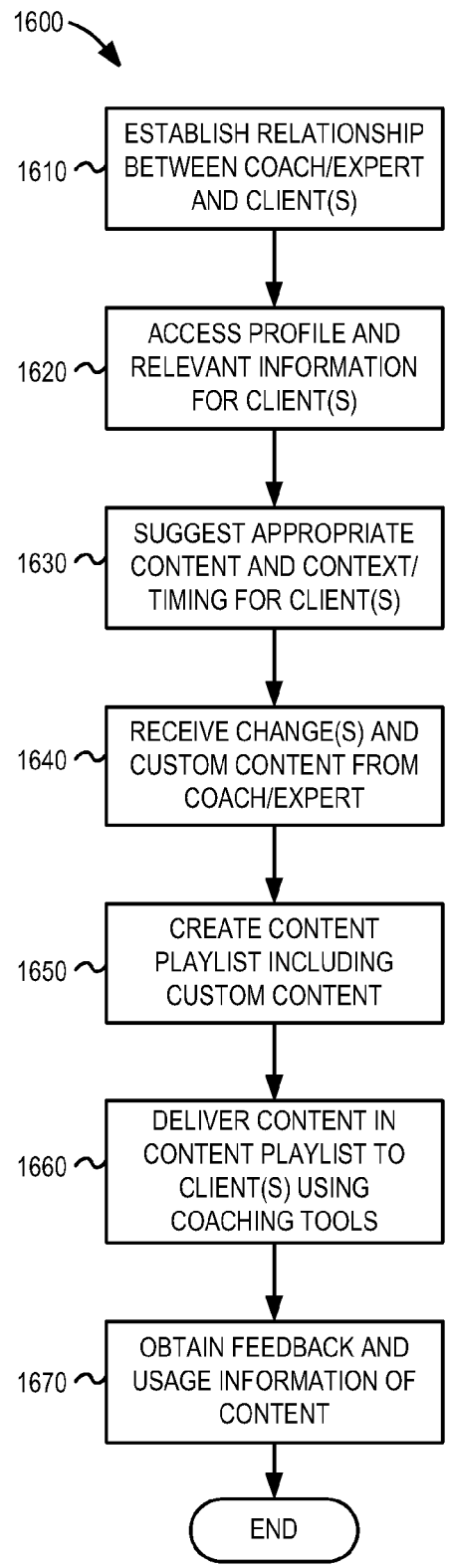
FIG. 16 illustrates an example method implementing creation and delivery of content to one or more client users from an expert or other coaching source according to an example described herein.

FIG. 16 illustrates a flowchart 1600 of an example implementation method of providing expert-based content and coaching from a professional user to a particular client or set of clients using the information system 100 according to an example described herein. The particular sequence depicted in the flowchart 1600 is provided as a non-limiting example, and illustrates a workflow involving a relationship between a coach/expert/other professional user and one or more clients. Other aspects of the workflow may include interactions with the previously described information system and associated databases and graphical user interfaces, with individual or groups of users.

The flowchart 1600 illustrates a series of operations including establishing a relationship between the professional user and one or more clients (operation 1610). The coaching operations may be assisted by accessing profile and relevant information for the one or more clients (operation 1620). From the profile and relevant information, the information system 100 may suggest appropriate content and content or timing for the one or more clients (operation 1630).

The professional user will provide changes and custom content to the information system (operation 1640). The information system 100 will use these changes and custom content to create a content playlist for the particular user(s) being coached by the professional user (operation 1650).

The information system 100 will deliver the content in the content playlist to the client(s) using coaching tools and various delivery mechanisms enabled by the information system (operation 1660). The information system 100 will then obtain feedback, responses, and other usage information of the client (operation 1670), for example to provide a response on the effectiveness of the coaching back to the professional user.

Although some of the previous examples were provided with reference to specific medical conditions and human activities such as weight loss and weight loss-related activities, it will be understood that the applicability of the present system may apply to a variety of human behaviors and goal-based activities in medical and non-medical settings. A non-limiting, illustrative listing of the applicability of the present techniques to medical conditions includes weight loss, smoking cessation, addition recovery, chronic illness management, psychological support, and the like. Another non-limiting, illustrative listing of the applicability of the present techniques includes application to non-medical settings such as education and learning, sport activities and sports training, and other scenarios where human activity is correlated to some goal or achievement.

Figure 17:
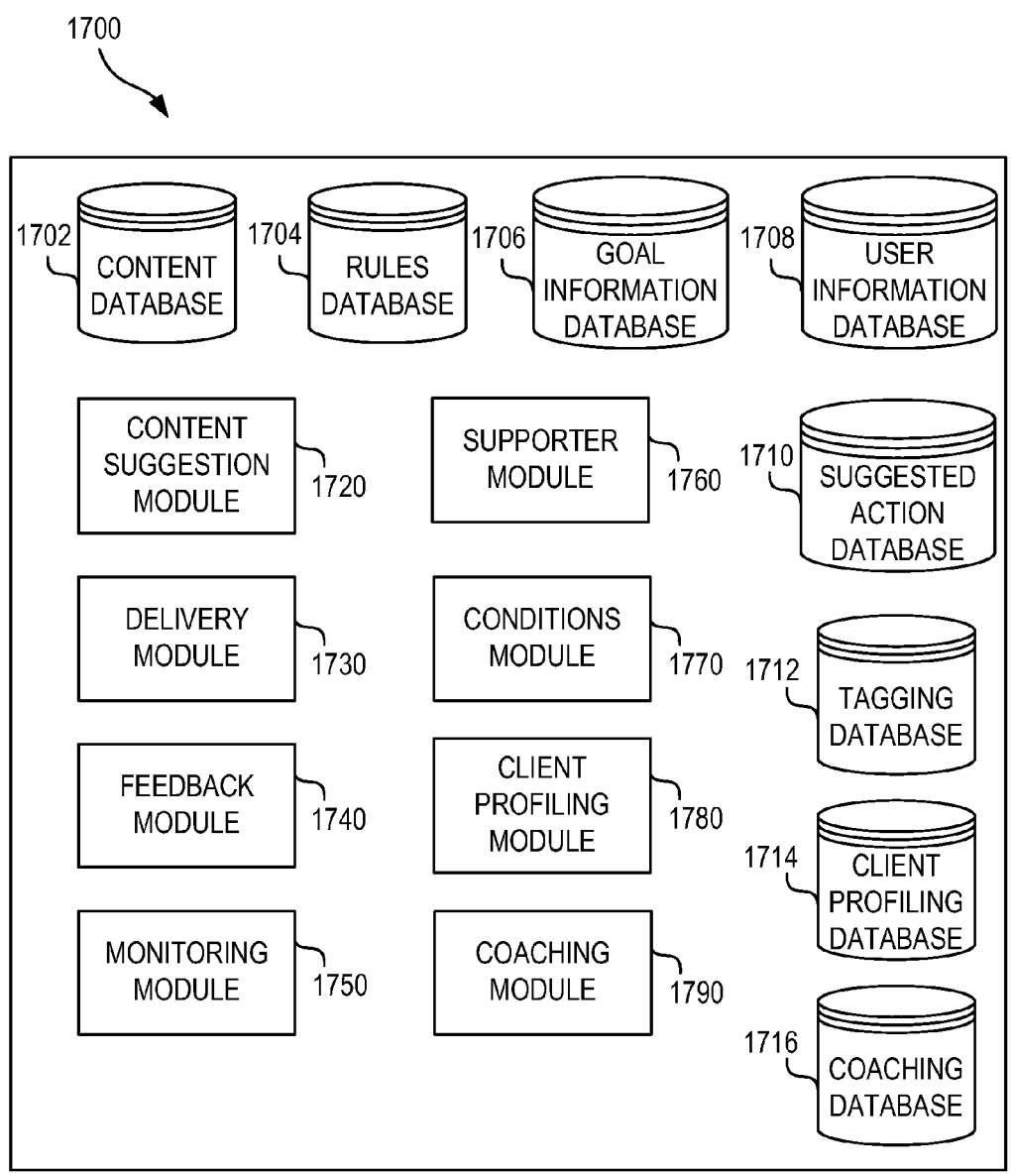
FIG. 17 illustrates an example system configuration of an information system arranged to provide suggested content according to an example described herein.

FIG. 17 illustrates an example of a system configuration of an information system 1700 configured to provide content. The information system 1700 may include a content database 1702, a rules database 1704, a goal information database 1706, a user information database 1708, a suggested action database 1710, a tagging database 1712, a client profiling database 1714, and a coaching database 1716.

The content database 1702 may include information from external sources, such as the supporter network 104, a professional expert working in a field relevant to a goal 204, other databases, or a combination thereof, among others. The rules database 1704 may include rules for formatting and providing personalized suggestions (e.g., suggested actions) to the client 106. Such rules may include timing restrictions, wording suggestions or restrictions, or suggested action restrictions (e.g., a suggestion with a certain tag should not be presented to a specific client, such as the client 106).

The goal information database 1706 may include data relevant to getting the client 106 to achieve a particular goal 204. The goal information may include certain activities that are a prerequisite to achieving a goal 204 (e.g., running a marathon requires the client to run to achieve the goal 204), recommended for achieving the goal 204 (e.g., stretching muscles and breathing exercises are helpful, but not essential, in training for a marathon), fun (e.g., things to keep the client 106 in a positive state of mind or reward the client 106 for their hard work or achievements), or a combination thereof, among others.

The user information database 1708 may include information gained from questionnaires or learned through the client 106 or supporters in the supporter network 104 using the system. The user information database 1708 may include information about all users of the system including supporters, clients 106, administrators of the system, or potential clients, among others. The suggested action database 1710 may include suggestions including pre statements, action statements, and post statements. The suggested action database 1710 may also include a record of which client has completed which suggestion, when the client 106 completed the suggestion, or how long it has been since the system recommended that suggestion to the client 106. The tagging database 1712 may include a record of all the tags and tagging relationships that have been created for suggestions, playlists, or programs, and which suggestions, programs, or playlists the tag is associated with.

The client profiling database 1714 may include information such as member profile information 400 described herein, and other client profiling information relevant to interactions with a professional user. The coaching database 1716 may include information on professional users, including feedback, stylizing templates, and other mechanisms to facilitate the generation and delivery of content from professional users.

While FIG. 17 shows eight separate databases 1702-1716, the information contained within the databases may be combined or divided to reside within any number of databases. For example, the information in the suggested action and tagging databases 1710, 1712 may be combined into a single database, or the user information and coaching databases 1708, 1716 may be combined into a single database.

The information system 1700 may include one or more modules including a content suggestion module 1720, a delivery module 1730, a feedback module 1740, a monitoring module 1750, a supporter module 1760, a conditions module 1770, a client profiling module 1780, and a coaching module 1790. The content suggestion module 1720 may receive suggestions or have access to the suggested action database 1710. The content suggestion module 1720 may include filter(s) and the weight(s), such as to allow the content suggestion module 1720 to filter, prioritize, or present suggestions to the client 106.

The delivery module 1730 may present at least one suggestion or message to the supporter network 104 or the client 106, such as at a certain relevant time. The delivery module 1730 may be configured to modify or amend the suggestion or message that is delivered so as to be appropriate for the client 106. Such a configuration may make the client 106 more likely to complete the suggestion.

The feedback module 1740 may be configured to receive feedback about suggestions from a client 106, process the feedback, and send the processed feedback to the user information database 1708, rules database 1704, content database 1702, or suggested action database 1710.

The monitoring module 1750 may be configured to monitor a client's progress towards their goal(s) 204, a client's progress on completing a suggestion, program, or playlist, and may provide the delivery module 1730 with information relevant to what messages (e.g., prompts, reminders, or encouragements) should be sent to the client 106.

The supporter module 1760 may be configured to provide the supporter network 104 with the ability to make suggestions for a suggestion to present to the client 106, provide information relevant to getting the client 106 to their goal 204 (e.g., likes, dislikes, barriers 214, or incentives 216 for the client 106, etc.), suggest messages to send to the client 106 that may be modified by the delivery module 1730, or suggest tags that should be associated with the client 106.

The conditions module 1770 may be configured to maintain relevant information from the ecosystem of conditions 212 and the client data conditions 108 that are relevant to the selection and delivery of relevant content. This may include direct or derived contextual data, or data relevant to barriers and incentives. For example, the contextual information maintained in conditions module 1770 may provide input for rules to express the conditions to deliver content to the proper user, at the proper time, in the proper context, and with the proper communication medium.

The client profiling module 1780 may be configured to collect client information such as the member profile information 400 described with reference to FIG. 4. The client profiling module may collect, compile, and monitor a variety data points used by a professional user for delivery of coaching-related content and assistance.

The coaching module 1790 may be configured to collect coaching information on the professional user and provide functions to initiate various interactions with the member client(s). These interactions may be facilitated through various communication mechanisms, content generation mechanisms, and mechanisms to assist the professional user with management of his or her personal network of client users.

Figure 18:
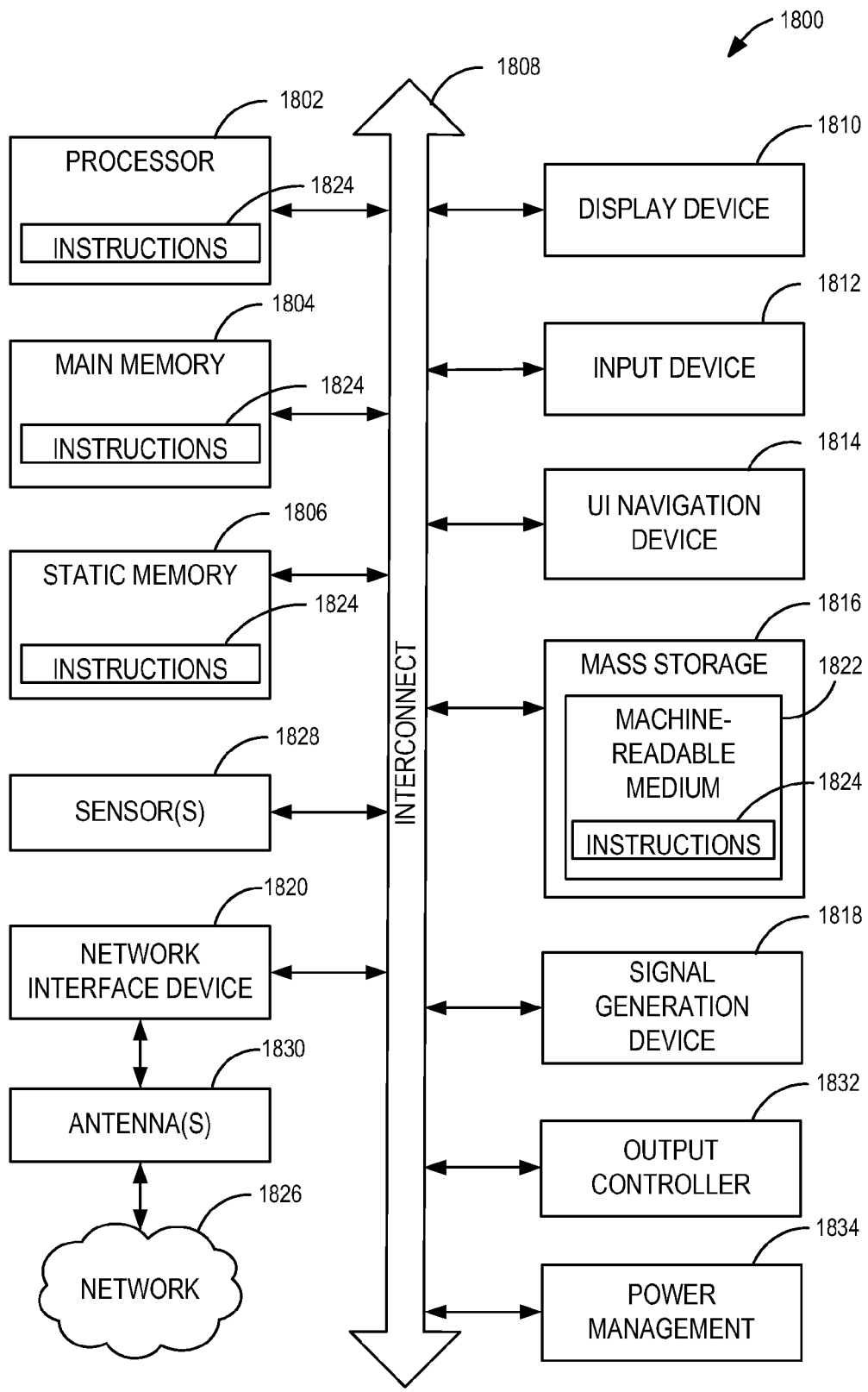
FIG. 18 illustrates an example of a computer system to implement techniques and system configurations according to an example described herein.

FIG. 18 is a block diagram illustrating an example computer system machine upon which any one or more of the methodologies herein discussed may be run. Computer system 1800 may be embodied as a computing device, providing operations of the suggestion engine 102, supporter network 104, information system 100 or interface components 1300 (from FIGS. 1 and 13), or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a set-top box (STB), a gaming console, a Personal Digital Assistant (PDA), a mobile telephone or smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1800 includes a processor 1802 (e.g., a central processing unit (CPU), a graphics processing unit (GPU) or both), a main memory 1804 and a static memory 1806, which communicate with each other via an interconnect 1808 (e.g., a link, a bus, etc.). The computer system 1800 may further include a video display unit 1810, an alphanumeric input device 1812 (e.g., a keyboard), and a user interface (UI) navigation device 1814 (e.g., a mouse). In one embodiment, the video display unit

1810, input device 1812 and UI navigation device 1814 are a touch screen display. The computer system 1800 may additionally include a storage device 1816 (e.g., a drive unit), a signal generation device 1818 (e.g., a speaker), an output controller 1832, a power management controller 1834, and a network interface device 1820 (which may include or operably communicate with one or more antennas 1830, transceivers, or other wireless communications hardware), and one or more sensors 1828, such as a GPS sensor, compass, location sensor, accelerometer, or other sensor.

The storage device 1816 includes a machine-readable medium 1822 on which is stored one or more sets of data structures and instructions 1824 (e.g., software) embodying or utilized by any one or more of the methodologies or functions described herein. The instructions 1824 may also reside, completely or at least partially, within the main memory 1804, static memory 1806, and/or within the processor 1802 during execution thereof by the computer system 1800, with the main memory 1804, static memory 1806, and the processor 1802 also constituting machine-readable media.

While the machine-readable medium 1822 is illustrated in an example embodiment to be a single medium, the term "machine-readable medium" may include a single medium or multiple media (e.g., a centralized or distributed database, and/or associated caches and servers) that store the one or more instructions 1824. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1824 may further be transmitted or received over a communications network 1826 using a transmission medium via the network interface device 1820 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the information system 100, 1700 may include or be embodied on a server running an operating system with software running thereon. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Embodiments may also be implemented as instructions stored on a computer-readable storage device or storage medium, which may be read and executed by at least one processor to perform the operations described herein. A computer-readable storage device or storage medium may include any non-transitory mechanism for storing information in a form readable by a machine (e.g., a computer). For example, a computer-readable storage device or storage medium may include read-only memory (ROM), random-access memory (RAM), magnetic disk storage media, optical storage media, flash-memory devices, and other storage devices and media. In some embodiments, the electronic devices and computing systems described herein may include one or more processors and may be configured with instructions stored on a computer-readable storage device.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Additional examples of the presently described method, system, and device embodiments include the following, non-limiting configurations. Each of the following non-limiting examples can stand on its own, or can be combined in any permutation or combination with any one or more of the other examples provided below, in the claims, or elsewhere in the present disclosure.

A first example can include the subject matter (such as an apparatus, a method, a means for performing acts, or a machine readable medium including instructions that, when performed by the machine, that can cause the machine to perform acts), for integrating guided coaching using an information system, including: accessing member profile information for a member user, the member profile information retrieved from a member profile database, and the member profile information being relevant to accomplishment of a goal set by the member user; obtaining suggested content for delivery to the member user based on the member profile information, the suggested content retrieved from a content database; receiving changes to the suggested content from a coaching user; and electronically delivering the suggested content to the member user, the delivering incorporating the changes to the suggested content received from the coaching user.

A second example can include, or can optionally be combined with the subject matter of the first example, to include subject matter (such as an apparatus, a method, a means for performing acts, or a machine readable medium including instructions that, when performed by the machine, that can cause the machine to perform acts), for an information system, including: a user information database storing information for a client user; a coaching database storing information for a coaching user; and a coaching module implemented using a processor, the coaching module configured to generate content for the client user that is received from the coaching user, and deliver the content to the client user, the content and a timing of delivery of the content customized to the user based on the information stored for the client user, wherein the content relates to an action to achieve a goal defined by the user.

A third example can include, or can optionally be combined with the subject matter of one or any combination of the first and second example, to include subject matter (such as an apparatus, a method, a means for performing acts, or a machine readable medium including instructions that, when performed by the machine, that can cause the machine to perform acts), for an computing device, configured to: generate a coaching content service interface for display within a coaching graphical user interface accessible by a coaching user, the coaching graphical user interface arranged to: display profile information for a client user; implement changes to coaching content selected for the client user; and receive a timing designation of coaching content for delivery to the client user; generate a client content service interface for display within a client graphical user interface accessible by the client user, the client graphical user interface arranged to: present the coaching content to the client user at the designated timing.

The following claims are hereby incorporated into the detailed description, with each claim and identified combination of claims standing on its own as a separate example.

What is claimed is:

1. A computer information system, comprising:
    data storage hardware, configured to provide:
        a user information database to store information for a client user; and
        a content database to store multiple content items; and
    processing hardware, operably coupled to the data storage hardware, the processing hardware configured by a plurality of machine-readable instructions being executed on the processing hardware, the processing hardware configured to provide:
        content suggestion processing circuitry to:
            access profile information for the client user, the profile information retrieved from the user information database, and the profile information being relevant to accomplishment of a goal that is set by the client user, wherein the goal is accomplished in connection with performance of a plurality of real-world activities by the client user;
            obtain suggested content from the content database for output to the client user based on the profile information, the suggested content including information to assist a performance of a particular activity of the plurality of real-world activities by the client user, wherein the suggested content is retrieved for the client user based on characteristics of the client user that are indicated in the profile information; and
            designate the suggested content for output to the client user at a specified output timing, the specified output timing of the output to the client user based on the characteristics of the client user that are indicated in the profile information and a determined likelihood of the performance of the particular activity by the client user;
        and
        coaching processing circuitry to:
            receive changes to the suggested content received from a coaching user, the changes to the suggested content received from an electronic device of the coaching user, wherein the changes to the suggested content include changes to the information of the suggested content or changes to the specified output timing, to encourage the performance of the particular activity by the client user; and
            electronically deliver the suggested content to an electronic device of the client user at the specified output timing, wherein the suggested content incorporates the changes to the information of the suggested content or the changes to the specified output timing received from the coaching user.

2. The computer information system of claim 1, wherein the data storage hardware is further configured to provide a client profiling database to store the profile information of the client user; and
    wherein the processing hardware is further configured to provide client profiling processing circuitry to collect the profile information of the client user and provide the profile information to the coaching processing circuitry.

3. The computer information system of claim 2, wherein the profile information maintained in the client profiling database includes archived data and current data for the client user relating to at least one of:
    demographic information, goal information, supporter information, activity information, restriction information, preference information, personality information, physiological information, communication preference information, timing information, environment information, or tracking information.

4. The computer information system of claim 2, wherein the processing hardware is further configured to provide:
    a monitoring processing circuitry to obtain real-time information related to the client user from a wearable tracking device of the client user; and
    a feedback processing circuitry to obtain feedback from the client user in response to the output of the suggested content to the client user.

5. The computer information system of claim 2, wherein the coaching processing circuitry is further to:
    access sensor data obtained from a wearable tracking device of the client user, wherein the sensor data is relevant to accomplishment of the goal that is set by the client user and includes a plurality of objective measurements for trackable activities;

wherein the suggested content is further retrieved for the client user based on the objective measurements for the trackable activities that are indicated in the sensor data, and wherein the specified output timing of the output to the client user is further based on the objective measurements for the trackable activities.

6. The computer information system of claim 2, wherein the content suggestion processing circuitry is further to:
electronically process sensor data obtained from a wearable tracking device of the client user, wherein the sensor data is relevant to accomplishment of the goal that is set by the client user and includes a plurality of objective measurements for the plurality of real-world activities;
generate a display of the plurality of objective measurements for the plurality of real-word activities for output in the electronic device of the coaching user, the plurality of objective measurements used by the coaching user to verify compliance of the performance of the plurality of real-world activities by the client user.

7. The computer information system of claim 2, wherein the data storage hardware is further configured to provide:
a tagging database to store tags associated with suggested actions of the suggested content; and
a suggested action database to store a playlist of multiple content items including the suggested actions; and
wherein the coaching processing circuitry is further to customize timing of output for the content items in the playlist of multiple content items, the suggested actions being selected for the client user based on a match of the tags associated with the suggested actions to the profile information.

8. The computer information system of claim 7, wherein the playlist of multiple content items includes multiple suggestions from the suggested action database being customized by the coaching user, and wherein the playlist of multiple content items includes a specification of timing, reminders, and motivators customized by the coaching user for respective of the content items.

9. The computer information system of claim 1, wherein the coaching processing circuitry is further to enable the coaching user to customize the suggested content, including to enable the coaching user to add a multimedia component to the suggested content or modify the suggested content using at least one of:
a content style, a sourcing characteristic, a ranking, a branding characteristic, an output style, or an output timing.

10. A non-transitory machine-readable storage medium comprising a plurality of instructions that, in response to being executed on a computing device, cause the computing device to:
access profile information for a client user, the profile information retrieved from a profile database, and the profile information being relevant to accomplishment of a goal that is set by the client user, wherein the goal is accomplished in connection with performance of a plurality of real-world activities by the client user;
obtain suggested content for output to the client user based on the profile information, the suggested content retrieved from a content database of an information system, the suggested content including information to assist a performance of a particular activity of the plurality of real-world activities by the client user, wherein the suggested content is retrieved for the client user based on characteristics of the client user that are indicated in the profile information;
designate the suggested content for output to the client user at a specified output timing, the specified output timing of the output to the client user based on the characteristics of the client user that are indicated in the profile information and a determined likelihood of the performance of the particular activity by the client user;
generate content to display within a coaching graphical user interface accessible by a coaching user, the coaching graphical user interface arranged to receive changes to the suggested content from the coaching user, wherein the changes to the suggested content are received from an electronic device of the coaching user, wherein the changes to the suggested content from the coaching user include changes to the information of the suggested content or changes to the specified output timing, to encourage the performance of the particular activity by the client user; and
generate content to display within a client graphical user interface accessible by the client user, the client graphical user interface arranged to electronically provide the suggested content on an electronic device of the client user at the specified output timing, wherein the client graphical user interface is further to incorporate the changes to the suggested content or the changes to the specified. output timing received from the coaching user.

11. The machine-readable storage medium of claim 10, wherein the instructions that cause the computing device to generate the content to display within the client graphical user interface further designate the suggested content into a content playlist for output at a designated timing, the content playlist used to deliver multiple reminders or motivators for obtaining a response to the suggested content.

12. The machine-readable storage medium of claim 11, wherein the instructions that cause the computing device to generate the content to display within the client graphical user interface further customize the suggested content and customize the output timing for the suggested content, based on an input from the coaching user to add multimedia content or apply a particular change to the suggested content, the particular change being applied for least one of:
a content style, a sourcing characteristic, a ranking, a branding characteristic, or an output style.

13. The machine-readable storage medium of claim 10, wherein the instructions that cause the computing device to generate the content to display within the coaching graphical user interface further implement at least a portion of the changes to the information of the suggested content received from the coaching user.

14. The machine-readable storage medium of claim 10, wherein new content provided from the coaching user is combined with the suggested content, the suggested content being generated from a content suggestion engine of the information system.

15. The machine-readable storage medium of claim 10, wherein the profile information includes archived data and current data relating to at least one of:
demographic information, goal information, supporter information, activity information, restriction information, preference information, personality information, physiological information, communication preference information, timing information, environment information, or tracking information.

16. The machine-readable storage medium of claim 10, wherein the instructions that cause the computing device to designate the suggested content for output to the client user at the specified output timing, further customize the specified output timing based on a match of tags associated with the suggested content to tags associated with the profile information.

17. The machine-readable storage medium of claim 16, wherein the plurality of instructions that cause the computing device to obtain suggested content for output to the client user based on the profile information include a selection of suggested content for the client user based on real-time information of user activity maintained in the profile information, the real-time information originating from an electronic device of the client user.

18. A method, performed by a computer information system, the method comprising a plurality of electronic operations performed upon processing hardware of the computer information system, with the electronic operations including:

accessing profile information associated with a human user, the profile information retrieved from a profile database of the computer information system, and the profile information being relevant to accomplishment of a goal that is established for the human user, wherein the goal is accomplished in connection with performance of a plurality of real-world activities by the human user;

accessing reporting information associated with the human user, the reporting information retrieved from a reporting database of the computer information system, and the reporting information originating from a reporting device that is operated by the human user, wherein the reporting device generates information about performance of at least one of the plurality of real-world activities by the human user as observed by the reporting device;

obtaining suggested content for output to the human user based on the profile information and the reporting information, the suggested content retrieved from a content database of the computer information system, the suggested content including content information to assist a performance of a particular activity of the plurality of real-world activities by the human user;

implementing customization to the suggested content, the customization to the suggested content originating from the computer information system or an electronic device that is operated by a coaching human user, wherein the customization to the suggested content includes a change to a specified output timing or a change to the content information, to encourage the performance of the particular activity by the human user; and electronically delivering the suggested content to an electronic output device of the human user, the suggested content to be output with the electronic output device at the specified output timing, and the suggested content incorporating the change to the content information or the change to the specified output timing.

19. The method of claim 18, wherein the reporting device is a wearable tracking device, wherein the wearable tracking device includes a sensor to collect sensor data, the electronic operations further including:

receiving sensor data from the wearable tracking device, the wearable tracking device being operated by the human user; and communicating the sensor data from the wearable tracking device to the coaching human user.

20. The method of claim 19, wherein the wearable tracking device further includes the electronic output device.

21. The method of claim 18, wherein the reporting device is a smartphone operated by the human user.

22. The method of claim 18, the electronic operations further including:

matching suggestions based on device data from a wearable tracking device operated by the human user, wherein the electronic operations for obtaining suggested content for output to the human user are performed in response to the suggestions being matched based on the device data from the wearable tracking device.

23. The method of claim 18, wherein receiving the customization to the suggested content from the coaching human user includes receiving additional content generated from the coaching human user to include in the change to the content information.

24. The method of claim 18, the electronic operations further including:

determining the specified output timing for output of the suggested content to the human user, the specified output timing determined based on the profile information and the reporting information.

25. The method of claim 18, the electronic operations further including:

determining the specified output timing for output of the suggested content to the human user, the specified output timing determined from characteristics of the human user that are indicated in the profile information and a determined likelihood of the performance of the particular activity by the human user.

26. The method of claim 18, wherein the profile information includes archived data and current data relating to at least one of:

demographic information, goal information, supporter information, activity information, restriction information, preference information, personality information, physiological information, communication preference information, timing information, environment information, or tracking information, for the human user.

27. The method of claim 18, wherein obtaining suggested content for output to the human user based on the profile information includes selecting suggested content for the human user based on real-time information of human user activity, the real-time information based on a most recent indication of data received from the reporting device of the human user.

* * * * *